United States Patent
Ortega et al.

(10) Patent No.: US 8,838,238 B2
(45) Date of Patent: *Sep. 16, 2014

(54) VENTRICULAR PACING

(71) Applicant: Cardiac Pacemakers, Inc., St. Paul, MN (US)

(72) Inventors: Daniel Felipe Ortega, Buenos Aires (AR); Alberto German Giniger, Buenos Aires (AR); Qingsheng Zhu, Wexford, PA (US); J. Edward Shapland, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/645,464

(22) Filed: Oct. 4, 2012

(65) Prior Publication Data

US 2013/0096638 A1 Apr. 18, 2013

Related U.S. Application Data

(63) Continuation of application No. 12/412,608, filed on Mar. 27, 2009, now Pat. No. 8,285,376, which is a continuation of application No. 11/300,611, filed on Dec. 13, 2005, now Pat. No. 7,512,440.

(30) Foreign Application Priority Data

Dec. 20, 2004 (AR) .............................. 20040104782

(51) Int. Cl.
*A61N 1/362* (2006.01)
(52) U.S. Cl.
USPC .............................................. 607/9

(58) Field of Classification Search
None
See application file for complete search history.

(56) References Cited

U.S. PATENT DOCUMENTS

| | | | |
|---|---|---|---|
| 3,614,955 A | 10/1971 | Mirowski, M. |
| 3,804,098 A | 4/1974 | Friedman |
| 3,866,615 A | 2/1975 | Hewson |
| 3,911,928 A | 10/1975 | Lagergren |

(Continued)

FOREIGN PATENT DOCUMENTS

| | | |
|---|---|---|
| DE | 2827595 A1 | 4/1979 |
| DE | 3712082 A1 | 10/1988 |

(Continued)

OTHER PUBLICATIONS

US 6,875,206, 4/2005, Ponzi (withdrawn).

(Continued)

*Primary Examiner* — Brian T Gedeon
(74) *Attorney, Agent, or Firm* — Schwegman Lundberg & Woessner, P.A.

(57) ABSTRACT

A method and apparatus are disclosed for treating a condition of a patient's heart includes placing a first electrode and/or a second electrode in a right ventricle of the heart. In one example, a reference electrode is placed within the patient and internal or external to the heart. A pacing signal is generated including a first signal component, a second signal component and a reference component with the first and second signal components having opposite polarity and with both of the first and second components having a potential relative to the reference component. The pacing signal and the placement of the electrodes are selected to alter a contraction of a left ventricle of the heart.

20 Claims, 12 Drawing Sheets

(56) References Cited

U.S. PATENT DOCUMENTS

| | | | |
|---|---|---|---|
| 3,942,536 A | 3/1976 | Mirowski et al. | |
| 3,949,757 A | 4/1976 | Sabel | |
| 3,995,623 A | 12/1976 | Blake et al. | |
| 4,026,303 A | 5/1977 | Babotai | |
| 4,030,508 A | 6/1977 | Thalen | |
| 4,057,067 A | 11/1977 | Lajos | |
| 4,106,512 A | 8/1978 | Bisping | |
| 4,136,703 A | 1/1979 | Wittkampf | |
| 4,154,247 A | 5/1979 | O'Neill | |
| 4,217,913 A | 8/1980 | Dutcher | |
| 4,258,725 A | 3/1981 | O'Neill | |
| 4,278,093 A | 7/1981 | Lafortune et al. | |
| 4,282,885 A | 8/1981 | Bisping | |
| 4,289,134 A | 9/1981 | Bernstein | |
| 4,289,144 A | 9/1981 | Gilman | |
| 4,311,153 A | 1/1982 | Smits | |
| 4,332,259 A | 6/1982 | McCorkle, Jr. | |
| 4,365,639 A | 12/1982 | Goldreyer | |
| 4,393,883 A | 7/1983 | Smyth et al. | |
| 4,402,329 A | 9/1983 | Williams | |
| 4,437,474 A | 3/1984 | Peers-Trevarton | |
| 4,458,677 A | 7/1984 | McCorkle, Jr. | |
| 4,458,695 A | 7/1984 | Peers-Trevarton | |
| 4,463,765 A | 8/1984 | Gold | |
| 4,469,104 A | 9/1984 | Peers-Trevarton | |
| 4,497,326 A | 2/1985 | Curry | |
| 4,540,236 A | 9/1985 | Peers-Trevarton | |
| 4,543,956 A | 10/1985 | Herscovici | |
| 4,549,548 A | 10/1985 | Wittkampf et al. | |
| 4,559,951 A | 12/1985 | Dahl et al. | |
| 4,567,901 A | 2/1986 | Harris | |
| 4,570,642 A | 2/1986 | Kane et al. | |
| 4,577,643 A | 3/1986 | Beranek | |
| 4,589,420 A | 5/1986 | Adams et al. | |
| 4,602,645 A | 7/1986 | Barrington et al. | |
| 4,603,705 A | 8/1986 | Speicher et al. | |
| 4,624,265 A | 11/1986 | Grassi | |
| 4,624,266 A | 11/1986 | Kane | |
| 4,627,439 A | 12/1986 | Harris | |
| 4,630,204 A | 12/1986 | Mortara | |
| 4,633,880 A | 1/1987 | Osypka et al. | |
| 4,641,649 A | 2/1987 | Walinsky et al. | |
| 4,643,201 A | 2/1987 | Stokes | |
| 4,646,755 A | 3/1987 | Kane | |
| 4,649,937 A | 3/1987 | DeHaan et al. | |
| 4,649,938 A | 3/1987 | McArthur | |
| 4,664,113 A | 5/1987 | Frisbie et al. | |
| 4,667,686 A | 5/1987 | Peers-Travarton | |
| H356 H | 11/1987 | Stokes et al. | |
| 4,721,115 A | 1/1988 | Owens | |
| 4,751,931 A | 6/1988 | Briller et al. | |
| 4,784,161 A | 11/1988 | Skalsky et al. | |
| 4,785,815 A | 11/1988 | Cohen | |
| 4,799,486 A | 1/1989 | DuFault | |
| 4,799,493 A | 1/1989 | DuFault | |
| 4,819,647 A | 4/1989 | Byers et al. | |
| 4,819,661 A | 4/1989 | Heil, Jr. et al. | |
| 4,819,662 A | 4/1989 | Heil, Jr. et al. | |
| 4,876,109 A | 10/1989 | Mayer et al. | |
| 4,886,074 A | 12/1989 | Bisping | |
| 4,892,102 A | 1/1990 | Astrinsky | |
| 4,895,152 A | 1/1990 | Callaghan et al. | |
| 4,922,607 A | 5/1990 | Doan et al. | |
| 4,922,927 A | 5/1990 | Fine et al. | |
| 4,924,881 A | 5/1990 | Brewer | |
| 4,953,564 A | 9/1990 | Berthelsen | |
| 4,967,766 A | 11/1990 | Bradshaw | |
| 4,972,848 A | 11/1990 | DiDomenico et al. | |
| 4,987,897 A | 1/1991 | Funke | |
| 4,994,078 A | 2/1991 | Jarvik | |
| 5,002,067 A | 3/1991 | Berthelsen et al. | |
| 5,007,864 A | 4/1991 | Stutz, Jr. | |
| 5,016,646 A | 5/1991 | Gotthardt et al. | |
| 5,036,848 A | 8/1991 | Hewson | |
| 5,050,601 A | 9/1991 | Kupersmith et al. | |
| 5,056,516 A | 10/1991 | Spehr | |
| 5,063,932 A | 11/1991 | Dahl et al. | |
| 5,076,285 A | 12/1991 | Hess et al. | |
| 5,083,564 A | 1/1992 | Scherlag | |
| 5,092,879 A | 3/1992 | Jarvik | |
| 5,129,404 A | 7/1992 | Spehr et al. | |
| 5,144,960 A | 9/1992 | Mehra et al. | |
| 5,152,299 A | 10/1992 | Soukup | |
| 5,174,289 A | 12/1992 | Cohen | |
| 5,179,962 A | 1/1993 | Dutcher et al. | |
| 5,181,511 A | 1/1993 | Nickolls et al. | |
| 5,223,226 A | 6/1993 | Wittmer et al. | |
| 5,242,430 A | 9/1993 | Arenas et al. | |
| 5,255,693 A | 10/1993 | Dutcher et al. | |
| 5,259,394 A | 11/1993 | Bens | |
| 5,259,395 A | 11/1993 | Li | |
| 5,267,560 A | 12/1993 | Cohen | |
| 5,275,620 A | 1/1994 | Darby et al. | |
| 5,282,845 A | 2/1994 | Bush et al. | |
| 5,299,569 A | 4/1994 | Wernicke et al. | |
| 5,300,108 A | 4/1994 | Rebell et al. | |
| 5,304,219 A | 4/1994 | Chernoff et al. | |
| 5,306,292 A | 4/1994 | Lindegren | |
| 5,313,953 A | 5/1994 | Yomtov et al. | |
| 5,320,642 A | 6/1994 | Scherlag | |
| 5,324,327 A | 6/1994 | Cohen | |
| 5,336,252 A | 8/1994 | Cohen | |
| 5,342,414 A | 8/1994 | Mehra | |
| 5,344,439 A | 9/1994 | Otten | |
| 5,358,516 A | 10/1994 | Myers et al. | |
| 5,366,496 A | 11/1994 | Dahl et al. | |
| 5,370,665 A * | 12/1994 | Hudrlik | 607/9 |
| 5,374,286 A | 12/1994 | Morris | |
| 5,381,790 A | 1/1995 | Kanesaka | |
| 5,393,929 A | 2/1995 | Yagihashi | |
| 5,405,373 A | 4/1995 | Petersson et al. | |
| 5,411,544 A | 5/1995 | Mar et al. | |
| 5,425,755 A | 6/1995 | Doan | |
| 5,433,735 A | 7/1995 | Zanakis et al. | |
| 5,439,391 A | 8/1995 | McEtchin et al. | |
| 5,447,533 A | 9/1995 | Vachon et al. | |
| 5,447,534 A | 9/1995 | Jammet | |
| 5,456,706 A | 10/1995 | Pless et al. | |
| 5,456,708 A | 10/1995 | Doan et al. | |
| 5,466,253 A | 11/1995 | Doan | |
| 5,476,497 A | 12/1995 | Mower et al. | |
| 5,476,499 A | 12/1995 | Hirschberg | |
| 5,476,501 A | 12/1995 | Stewart et al. | |
| 5,476,502 A | 12/1995 | Rubin | |
| 5,492,119 A | 2/1996 | Abrams | |
| 5,500,008 A | 3/1996 | Fain | |
| 5,514,172 A | 5/1996 | Mueller | |
| 5,515,848 A | 5/1996 | Corbett, III et al. | |
| 5,522,874 A | 6/1996 | Gates | |
| 5,524,338 A | 6/1996 | Martyniuk et al. | |
| 5,527,344 A | 6/1996 | Arzbaecher et al. | |
| 5,531,780 A | 7/1996 | Vachon | |
| 5,545,201 A | 8/1996 | Helland et al. | |
| 5,554,178 A | 9/1996 | Dahl et al. | |
| 5,571,163 A | 11/1996 | Helland | |
| 5,578,068 A | 11/1996 | Laske et al. | |
| 5,593,405 A | 1/1997 | Osypka | |
| 5,593,433 A | 1/1997 | Spehr et al. | |
| 5,609,158 A | 3/1997 | Chan | |
| 5,628,778 A | 5/1997 | Kruse et al. | |
| 5,628,779 A | 5/1997 | Bornzin et al. | |
| 5,634,829 A | 6/1997 | Kerul | |
| 5,634,899 A | 6/1997 | Shapland et al. | |
| 5,674,272 A | 10/1997 | Bush et al. | |
| 5,674,274 A | 10/1997 | Morgan et al. | |
| 5,683,447 A | 11/1997 | Bush et al. | |
| 5,702,427 A | 12/1997 | Ecker et al. | |
| 5,709,753 A | 1/1998 | Olson et al. | |
| 5,716,390 A | 2/1998 | Li | |
| 5,718,720 A | 2/1998 | Prutchi et al. | |
| 5,720,099 A | 2/1998 | Parker et al. | |
| 5,728,140 A | 3/1998 | Salo et al. | |
| 5,733,323 A | 3/1998 | Buck et al. | |
| 5,755,766 A | 5/1998 | Chastain et al. | |

(56) References Cited

U.S. PATENT DOCUMENTS

| | | |
|---|---|---|
| 5,769,881 A | 6/1998 | Schroeppel et al. |
| 5,772,693 A | 6/1998 | Brownlee |
| 5,782,898 A | 7/1998 | Dahl et al. |
| 5,800,464 A | 9/1998 | Kieval |
| 5,800,465 A | 9/1998 | Thompson et al. |
| 5,807,306 A | 9/1998 | Shapland et al. |
| 5,810,887 A | 9/1998 | Accorti, Jr. et al. |
| 5,814,077 A | 9/1998 | Sholder et al. |
| 5,814,079 A | 9/1998 | Kieval |
| 5,851,227 A | 12/1998 | Spehr |
| 5,861,013 A | 1/1999 | Peck et al. |
| 5,871,506 A | 2/1999 | Mower |
| 5,871,529 A | 2/1999 | Bartig et al. |
| 5,871,531 A | 2/1999 | Struble |
| 5,876,399 A | 3/1999 | Chia et al. |
| 5,876,431 A | 3/1999 | Spehr et al. |
| 5,916,214 A | 6/1999 | Cosio et al. |
| 5,925,045 A | 7/1999 | Reimels et al. |
| 5,935,159 A | 8/1999 | Cross, Jr. et al. |
| 5,941,868 A | 8/1999 | Kaplan et al. |
| 5,944,710 A | 8/1999 | Dev et al. |
| 5,964,795 A | 10/1999 | McVenes et al. |
| 5,972,416 A | 10/1999 | Reimels et al. |
| 5,995,871 A | 11/1999 | Knisley |
| 6,006,139 A | 12/1999 | Kruse et al. |
| 6,007,476 A | 12/1999 | Wascher et al. |
| 6,024,739 A | 2/2000 | Ponzi et al. |
| 6,059,726 A | 5/2000 | Lee et al. |
| 6,070,104 A | 5/2000 | Hine et al. |
| 6,086,582 A | 7/2000 | Altman et al. |
| 6,096,069 A | 8/2000 | Bischoff |
| 6,123,084 A | 9/2000 | Jandak et al. |
| 6,141,588 A | 10/2000 | Cox et al. |
| 6,141,594 A | 10/2000 | Flynn et al. |
| 6,144,879 A | 11/2000 | Gray |
| 6,161,029 A | 12/2000 | Spreigl et al. |
| 6,165,164 A | 12/2000 | Hill et al. |
| 6,212,434 B1 | 4/2001 | Scheiner et al. |
| 6,219,581 B1 | 4/2001 | Schaldach et al. |
| 6,230,061 B1 | 5/2001 | Hartung |
| 6,236,887 B1 | 5/2001 | Ben-Haim et al. |
| 6,254,573 B1 | 7/2001 | Haim et al. |
| 6,256,541 B1 | 7/2001 | Heil et al. |
| 6,267,778 B1 | 7/2001 | Cohen |
| 6,309,370 B1 | 10/2001 | Haim et al. |
| 6,341,235 B1 | 1/2002 | Mower |
| 6,345,204 B1 | 2/2002 | Scheiner et al. |
| 6,358,247 B1 | 3/2002 | Altman et al. |
| 6,363,286 B1 | 3/2002 | Zhu et al. |
| 6,416,510 B1 | 7/2002 | Altman et al. |
| 6,430,441 B1 | 8/2002 | Levine |
| 6,463,334 B1 | 10/2002 | Flynn et al. |
| 6,468,263 B1 | 10/2002 | Fischell et al. |
| 6,471,697 B1 | 10/2002 | Lesh |
| 6,484,057 B2 | 11/2002 | Ideker et al. |
| 6,505,082 B1 | 1/2003 | Scheiner et al. |
| 6,535,766 B1 | 3/2003 | Thompson et al. |
| 6,540,725 B1 | 4/2003 | Ponzi |
| 6,542,775 B2 | 4/2003 | Ding et al. |
| 6,544,270 B1 | 4/2003 | Zhang |
| 6,547,787 B1 | 4/2003 | Altman et al. |
| 6,556,874 B2 | 4/2003 | Audoglio |
| 6,560,489 B2 | 5/2003 | Hauck |
| 6,575,931 B1 | 6/2003 | Ponzi |
| 6,585,716 B2 | 7/2003 | Altman |
| 6,606,517 B1 | 8/2003 | Park et al. |
| 6,609,027 B2 | 8/2003 | Kroll et al. |
| 6,623,473 B1 | 9/2003 | Ponzi |
| 6,623,474 B1 | 9/2003 | Ponzi |
| 6,643,546 B2 | 11/2003 | Mathis et al. |
| 6,650,940 B1 | 11/2003 | Zhu et al. |
| 6,702,744 B2 | 3/2004 | Mandrusov et al. |
| 6,702,777 B2 | 3/2004 | Haim et al. |
| 6,718,206 B2 | 4/2004 | Casavant |
| 6,766,190 B2 | 7/2004 | Ferek-Petric |
| 6,768,923 B2 | 7/2004 | Ding et al. |
| 6,801,807 B2 | 10/2004 | Abrahamson |
| 6,804,555 B2 | 10/2004 | Warkentin |
| 6,810,286 B2 | 10/2004 | Donovan et al. |
| 6,855,124 B1 | 2/2005 | Gonzalez et al. |
| 6,901,289 B2 | 5/2005 | Dahl et al. |
| 6,904,316 B2 | 6/2005 | Kramer |
| 6,905,476 B2 | 6/2005 | Ponzi |
| 6,907,285 B2 | 6/2005 | Denker et al. |
| 6,909,920 B2 | 6/2005 | Lokhoff et al. |
| 6,915,169 B2 | 7/2005 | Flynn et al. |
| 6,931,286 B2 | 8/2005 | Sigg et al. |
| 6,937,897 B2 | 8/2005 | Min et al. |
| 7,027,866 B2 | 4/2006 | Warkentin et al. |
| 7,027,876 B2 | 4/2006 | Casavant et al. |
| 7,039,462 B2 | 5/2006 | Pastore et al. |
| 7,096,051 B1 | 8/2006 | Alder |
| 7,113,825 B2 | 9/2006 | Pastore et al. |
| 7,130,682 B2 | 10/2006 | Stahmann et al. |
| 7,187,970 B2 | 3/2007 | Shemer et al. |
| 7,245,973 B2 | 7/2007 | Liu et al. |
| 7,257,443 B2 | 8/2007 | Pastore et al. |
| 7,280,872 B1 | 10/2007 | Mosesov et al. |
| 7,317,950 B2 | 1/2008 | Lee |
| 7,319,900 B2 | 1/2008 | Kim et al. |
| 7,359,837 B2 | 4/2008 | Drew |
| 7,392,095 B2 | 6/2008 | Flynn et al. |
| 7,395,042 B2 | 7/2008 | Alder |
| 7,400,931 B2 | 7/2008 | Mandrusov et al. |
| 7,457,664 B2 | 11/2008 | Zhang et al. |
| 7,460,914 B2 | 12/2008 | Mandrusov et al. |
| 7,509,170 B2 | 3/2009 | Zhang et al. |
| 7,512,440 B2 | 3/2009 | Ortega et al. |
| 7,529,584 B2 | 5/2009 | Laske et al. |
| 7,792,580 B2 | 9/2010 | Borowitz et al. |
| 7,817,784 B2 | 10/2010 | Wang et al. |
| 8,005,544 B2 | 8/2011 | Zhu et al. |
| 8,010,191 B2 | 8/2011 | Zhu et al. |
| 8,010,192 B2 | 8/2011 | Zhu et al. |
| 8,014,861 B2 | 9/2011 | Zhu et al. |
| 8,050,756 B2 | 11/2011 | Zhu et al. |
| 8,078,287 B2 | 12/2011 | Liu et al. |
| 8,285,376 B2 | 10/2012 | Ortega et al. |
| 8,290,586 B2 | 10/2012 | Zhu et al. |
| 8,326,423 B2 | 12/2012 | Zhu et al. |
| 8,346,358 B2 | 1/2013 | Ortega et al. |
| 8,423,139 B2 | 4/2013 | Zhu et al. |
| 8,428,715 B2 | 4/2013 | Ortega et al. |
| 8,437,848 B2 | 5/2013 | Ortega et al. |
| 8,538,521 B2 | 9/2013 | Zhu et al. |
| 8,543,203 B2 | 9/2013 | Zhu et al. |
| 8,565,880 B2 | 10/2013 | Dong et al. |
| 2001/0031986 A1 | 10/2001 | Hauck |
| 2001/0044619 A1 | 11/2001 | Altman |
| 2002/0010492 A1 | 1/2002 | Donovan et al. |
| 2002/0016615 A1 | 2/2002 | Dev et al. |
| 2002/0022863 A1 | 2/2002 | Hauck |
| 2002/0026228 A1 | 2/2002 | Schauerte |
| 2002/0049478 A1 | 4/2002 | Ding et al. |
| 2002/0058981 A1 | 5/2002 | Zhu et al. |
| 2002/0099413 A1 | 7/2002 | Mower |
| 2002/0120318 A1 | 8/2002 | Kroll et al. |
| 2002/0169484 A1 | 11/2002 | Mathis et al. |
| 2002/0183720 A1 | 12/2002 | Hill et al. |
| 2002/0193836 A1 | 12/2002 | Schmidt |
| 2002/0198583 A1 | 12/2002 | Rock et al. |
| 2003/0009145 A1 | 1/2003 | Struijker-Boudier et al. |
| 2003/0032938 A1 | 2/2003 | Altman |
| 2003/0069625 A1 | 4/2003 | Ley et al. |
| 2003/0078625 A1 | 4/2003 | Casavant |
| 2003/0083700 A1 | 5/2003 | Hill |
| 2003/0083711 A1 | 5/2003 | Yonce et al. |
| 2003/0093104 A1 | 5/2003 | Bonner et al. |
| 2003/0105492 A1 | 6/2003 | Ding et al. |
| 2003/0105496 A1 | 6/2003 | Yu et al. |
| 2003/0109914 A1 | 6/2003 | Westlund et al. |
| 2003/0113303 A1 | 6/2003 | Schwartz |
| 2003/0125615 A1 | 7/2003 | Schwartz |
| 2003/0129750 A1 | 7/2003 | Schwartz |

(56) References Cited

U.S. PATENT DOCUMENTS

| | | |
|---|---|---|
| 2003/0163184 A1 | 8/2003 | Scheiner et al. |
| 2003/0171723 A1 | 9/2003 | Ponzi |
| 2003/0195470 A1 | 10/2003 | Ponzi |
| 2004/0006265 A1 | 1/2004 | Alhussiny |
| 2004/0064176 A1 | 4/2004 | Min et al. |
| 2004/0098057 A1 | 5/2004 | Pastore et al. |
| 2004/0104782 A1 | 6/2004 | Ruffieux |
| 2004/0106958 A1 | 6/2004 | Mathis et al. |
| 2004/0122484 A1 | 6/2004 | Hatlestad et al. |
| 2004/0153127 A1 | 8/2004 | Gordon et al. |
| 2004/0186546 A1 | 9/2004 | Mandrusov et al. |
| 2004/0193223 A1 | 9/2004 | Kramer et al. |
| 2004/0213770 A1 | 10/2004 | Seward et al. |
| 2004/0214182 A1 | 10/2004 | Sharma et al. |
| 2004/0215240 A1 | 10/2004 | Lovett et al. |
| 2004/0215249 A1 | 10/2004 | Corbucci |
| 2004/0215251 A1 | 10/2004 | Sharma et al. |
| 2004/0260374 A1 | 12/2004 | Zhang et al. |
| 2005/0049516 A1 | 3/2005 | Ideker |
| 2005/0075677 A1 | 4/2005 | Ganion et al. |
| 2005/0102002 A1 | 5/2005 | Salo et al. |
| 2005/0125041 A1 | 6/2005 | Min et al. |
| 2005/0136385 A1 | 6/2005 | Mann |
| 2005/0137671 A1 | 6/2005 | Liu et al. |
| 2005/0152516 A1 | 7/2005 | Wang et al. |
| 2005/0159725 A1 | 7/2005 | Tockman et al. |
| 2005/0203580 A1 | 9/2005 | Prentice et al. |
| 2005/0267557 A1 | 12/2005 | Flynn et al. |
| 2005/0277993 A1 | 12/2005 | Mower |
| 2006/0030810 A1 | 2/2006 | Mandrusov et al. |
| 2006/0064027 A1 | 3/2006 | Borowitz et al. |
| 2006/0104596 A1 | 5/2006 | Askins et al. |
| 2006/0116596 A1 | 6/2006 | Zhou et al. |
| 2006/0136001 A1 | 6/2006 | Ortega et al. |
| 2006/0142812 A1 | 6/2006 | Ortega et al. |
| 2006/0224197 A1 | 10/2006 | Havel et al. |
| 2006/0224224 A1 | 10/2006 | Muhlenberg et al. |
| 2006/0253156 A1 | 11/2006 | Pastore et al. |
| 2007/0027488 A1 | 2/2007 | Kaiser et al. |
| 2007/0060961 A1 | 3/2007 | Echt et al. |
| 2007/0093872 A1 | 4/2007 | Chirife et al. |
| 2007/0093874 A1 | 4/2007 | Chirife et al. |
| 2007/0100380 A1 | 5/2007 | Fukui |
| 2007/0129764 A1 | 6/2007 | Burnes |
| 2007/0208387 A1 | 9/2007 | Mower |
| 2007/0232949 A1 | 10/2007 | Saksena |
| 2007/0233216 A1 | 10/2007 | Liu et al. |
| 2007/0239219 A1 | 10/2007 | Salo et al. |
| 2008/0234771 A1 | 9/2008 | Chinchoy et al. |
| 2008/0262587 A1 | 10/2008 | Flynn et al. |
| 2008/0288030 A1 | 11/2008 | Zhang et al. |
| 2008/0319496 A1 | 12/2008 | Zhu et al. |
| 2008/0319499 A1 | 12/2008 | Zhu et al. |
| 2008/0319500 A1 | 12/2008 | Zhu et al. |
| 2008/0319501 A1 | 12/2008 | Zhu et al. |
| 2009/0005830 A1 | 1/2009 | Zhu et al. |
| 2009/0005832 A1 | 1/2009 | Zhu et al. |
| 2009/0005846 A1 | 1/2009 | Zhu et al. |
| 2009/0054942 A1 | 2/2009 | Zhu et al. |
| 2009/0093859 A1 | 4/2009 | Ortega et al. |
| 2009/0093861 A1 | 4/2009 | Ortega et al. |
| 2009/0099619 A1 | 4/2009 | Lessmeier et al. |
| 2009/0105778 A1 | 4/2009 | Lee et al. |
| 2009/0259272 A1 | 10/2009 | Reddy et al. |
| 2010/0042176 A1 | 2/2010 | Snell |
| 2010/0318147 A1 | 12/2010 | Forslund et al. |
| 2011/0264158 A1 | 10/2011 | Dong et al. |
| 2011/0264168 A1 | 10/2011 | Dadd et al. |
| 2011/0307026 A1 | 12/2011 | Zhu et al. |
| 2011/0319956 A1 | 12/2011 | Zhu et al. |
| 2012/0041500 A1 | 2/2012 | Zhu et al. |
| 2012/0041503 A1 | 2/2012 | Zhu et al. |
| 2012/0053651 A1 | 3/2012 | Zhu et al. |
| 2012/0101539 A1 | 4/2012 | Zhu et al. |
| 2012/0239106 A1 | 9/2012 | Maskara et al. |
| 2013/0041423 A1 | 2/2013 | Zhu et al. |
| 2013/0184774 A1 | 7/2013 | Zhu et al. |
| 2013/0261689 A1 | 10/2013 | Zhu et al. |
| 2013/0261690 A1 | 10/2013 | Ortega et al. |
| 2014/0018871 A1 | 1/2014 | Zhu et al. |
| 2014/0018874 A1 | 1/2014 | Zhu et al. |

FOREIGN PATENT DOCUMENTS

| | | |
|---|---|---|
| EP | 042551 A1 | 12/1981 |
| EP | 0057877 A1 | 8/1982 |
| EP | 0282047 A2 | 9/1988 |
| EP | 0321764 A1 | 6/1989 |
| EP | 0452278 A2 | 10/1991 |
| EP | 0573275 A2 | 12/1993 |
| EP | 0591053 A1 | 4/1994 |
| EP | 0612538 A2 | 8/1994 |
| EP | 0620024 A1 | 10/1994 |
| EP | 0672431 A2 | 9/1995 |
| EP | 0709111 A2 | 5/1996 |
| EP | 1234597 A2 | 8/2002 |
| EP | 18309020 A1 | 9/2007 |
| EP | 2164560 A1 | 2/2010 |
| EP | 2164561 A2 | 3/2010 |
| EP | 2164562 A1 | 3/2010 |
| EP | 1830920 B1 | 10/2013 |
| FR | 2465489 A1 | 3/1981 |
| FR | 2575925 A1 | 7/1986 |
| FR | 2757773 A1 | 7/1998 |
| GB | 2240721 A | 8/1991 |
| JP | 5501211 A | 3/1993 |
| JP | 06312025 A | 11/1994 |
| JP | 10052507 A | 2/1998 |
| JP | 2004351122 A | 12/2004 |
| JP | 2005507720 A | 3/2005 |
| JP | 2008523950 A | 7/2008 |
| JP | 2008539894 A | 11/2008 |
| JP | 2012512727 A | 6/2012 |
| WO | WO-9220401 A1 | 11/1992 |
| WO | WO-9422525 A1 | 10/1994 |
| WO | WO-9615665 A2 | 5/1996 |
| WO | WO-9740883 A1 | 11/1997 |
| WO | WO-0074773 A1 | 12/2000 |
| WO | WO-0335170 A1 | 5/2003 |
| WO | WO-03035170 A1 | 5/2003 |
| WO | WO-2005011475 A2 | 2/2005 |
| WO | WO-2006068880 A1 | 6/2006 |
| WO | WO-2006115659 A1 | 11/2006 |
| WO | WO-2008063498 A1 | 5/2008 |
| WO | WO-2009006321 A2 | 1/2009 |
| WO | WO-2009006325 A1 | 1/2009 |
| WO | WO-2009006327 A1 | 1/2009 |
| WO | WO-2009006331 A1 | 1/2009 |
| WO | WO-2009006339 A1 | 1/2009 |
| WO | WO-2009078751 A1 | 6/2009 |
| WO | WO-2010042910 A1 | 4/2010 |
| WO | WO-2010071849 A2 | 6/2010 |
| WO | WO-2010071849 A3 | 8/2010 |
| WO | WO-2011139691 A1 | 11/2011 |
| WO | WO-2012125273 A2 | 9/2012 |
| WO | WO-2012125273 A3 | 9/2012 |

OTHER PUBLICATIONS

"U.S. Appl. No. 10/004,695, Response filed Mar. 9, 2004 to Non-Final Office Action mailed Dec. 22, 2003", 8 pgs.

"U.S. Appl. No. 10/745,302, Non-Final Office Action mailed Mar. 14, 2006", 19 pgs.

"U.S. Appl. No. 10/745,302, Non-Final Office Action mailed Sep. 14, 2006", 14 pgs.

"U.S. Appl. No. 10/745,302, Non-Final Office Action mailed Sep. 23, 2005", 11 pgs.

"U.S. Appl. No. 10/745,302, Notice of Allowance mailed Mar. 12, 2007", 4 pgs.

"U.S. Appl. No. 10/745,302, Response filed Jun. 26, 2006 to Non Final Office Action mailed Mar. 14, 2006", 16 pgs.

"U.S. Appl. No. 10/745,302, Response filed Sep. 12, 2005 to Restriction Requirement Mailed Aug. 12, 2005", 6 pgs.

(56) References Cited

OTHER PUBLICATIONS

"U.S. Appl. No. 10/745,302, Response filed Dec. 14, 2006 to Non Final Office Action mailed Sep. 14, 2006", 13 pgs.
"U.S. Appl. No. 10/745,302, Response filed Dec. 23, 2005 to Non Final Office Action mailed Sep. 23, 2005", 15 pgs.
"U.S. Appl. No. 10/745,302, Restriction Requirement mailed Aug. 12, 2005", 7 pgs.
"U.S. Appl. No. 11/300,242, Final Office Action mailed Aug. 4, 2009", 9 pgs.
"U.S. Appl. No. 11/300,242, Non Final Office Action mailed May 12, 2011", 9 pgs.
"U.S. Appl. No. 11/300,242, Non-Final Office Action mailed Mar. 27, 2008", 8 pgs.
"U.S. Appl. No. 11/300,242, Notice of Allowance mailed Jan. 24, 2012", 5 pgs.
"U.S. Appl. No. 11/300,242, Response filed Feb. 4, 2010 to Final Office Action mailed Aug. 4, 2009", 11 pgs.
"U.S. Appl. No. 11/300,242, Response filed Apr. 2, 2009 to Restriction Requirement mailed Dec. 15, 2008", 8 pgs.
"U.S. Appl. No. 11/300,242, Response filed Sep. 12, 2011 to Non Final Office Action mailed May 12, 2011", 8 pgs.
"U.S. Appl. No. 11/300,242, Response filed Sep. 26, 2008 to Non-Final Office Action mailed Mar. 27, 2008", 10 pgs.
"U.S. Appl. No. 11/300,242, Restriction Requirement mailed Dec. 15, 2008", 10 pgs.
"U.S. Appl. No. 11/300,611, 312 Amendment filed Feb. 9, 2009", 9 pgs.
"U.S. Appl. No. 11/300,611, Non-Final Office Action mailed Mar. 20, 2008", 7 pgs.
"U.S. Appl. No. 11/300,611, Notice of Allowance mailed Jan. 26, 2009", 7 pgs.
"U.S. Appl. No. 11/300,611, PTO Response to 312 Amendment mailed Feb. 26, 2009", 3 pgs.
"U.S. Appl. No. 11/300,611, Response filed Sep. 22, 2008 to Non-Final Office Action mailed Mar. 20, 2008", 12 pgs.
"U.S. Appl. No. 12/147,293, Notice of Allowance mailed Apr. 8, 2011", 12 pgs.
"U.S. Appl. No. 12/147,293, Response filed Feb. 8, 2011 to Restriction Requirement mailed Oct. 8, 2010", 9 pgs.
"U.S. Appl. No. 12/147,293, Restriction Requirement mailed Oct. 8, 2010", 12 pgs.
"U.S. Appl. No. 12/147,317, Examiner Interview Summary mailed Mar. 15, 2011", 3 pgs.
"U.S. Appl. No. 12/147,317, Final Office Action mailed Oct. 12, 2011", 6 pgs.
"U.S. Appl. No. 12/147,317, Non-Final Office Action mailed Dec. 28, 2010", 7 pgs.
"U.S. Appl. No. 12/147,317, Response filed Apr. 11, 2012 to Final Office Action mailed Oct. 12, 2011", 8 pgs.
"U.S. Appl. No. 12/147,317, Response filed Jun. 27, 2011 to Non Final Office Action mailed Dec. 28, 2010", 11 pgs.
"U.S. Appl. No. 12/147,339, Notice of Allowance mailed Mar. 30, 2011", 9 pgs.
"U.S. Appl. No. 12/147,339, Notice of Allowance mailed Dec. 22, 2010", 8 pgs.
"U.S. Appl. No. 12/147,339, Response filed Oct. 20, 2010 to Restriction Requirement mailed Oct. 8, 2010", 7 pgs.
"U.S. Appl. No. 12/147,339, Restriction Requirement mailed Oct. 8, 2010", 7 pgs.
"U.S. Appl. No. 12/147,356, Notice of Allowance mailed Feb. 10, 2011", 17 pgs.
"U.S. Appl. No. 12/147,356, Notice of Allowance mailed Jun. 30, 2011", 15 pgs.
"U.S. Appl. No. 12/147,356, Response filed Nov. 10, 2010 to Restriction Requirement mailed Oct. 12, 2010", 9 pgs.
"U.S. Appl. No. 12/147,356, Restriction Requirement mailed Oct. 12, 2010", 7 pgs.
"U.S. Appl. No. 12/147,369, Non-Final Office Action mailed Sep. 10, 2010", 10 pgs.

"U.S. Appl. No. 12/147,369, Notice of Allowance mailed Apr. 21, 2011", 7 pgs.
"U.S. Appl. No. 12/147,369, Response filed Feb. 10, 2011 to Non Final Office Action mailed Sep. 10, 2010", 7 pgs.
"U.S. Appl. No. 12/147,376, Final Office Action mailed Apr. 20, 2011", 11 pgs.
"U.S. Appl. No. 12/147,376, Non Final Office Action mailed Oct. 3, 2011", 8 pgs.
"U.S. Appl. No. 12/147,376, Non-Final Office Action mailed Sep. 15, 2010", 9 pgs.
"U.S. Appl. No. 12/147,376, Notice of Allowance mailed Mar. 19, 2012", 7 pgs.
"U.S. Appl. No. 12/147,376, Response filed Feb. 15, 2011 to Non Final Office Action mailed Sep. 15, 2010", 9 pgs.
"U.S. Appl. No. 12/147,376, Response filed Feb. 29, 2012 to Non Final Office Action mailed Oct. 3, 2011", 6 pgs.
"U.S. Appl. No. 12/147,376, Response filed Aug. 22, 2011 to Final Office Action mailed Apr. 20, 2011", 8 pgs.
"U.S. Appl. No. 12/147,376, Non-Final Office Action mailed Sep. 15, 2010", 10 pgs.
"U.S. Appl. No. 12/147,425, Notice of Allowance mailed Apr. 19, 2011", 8 pgs.
"U.S. Appl. No. 12/147,425, Response filed Feb. 15, 2011 to Non Final Office Action mailed Sep. 15, 2010", 8 pgs.
"U.S. Appl. No. 12/249,454, Examiner Interview Summary mailed Feb. 22, 2012", 3 pgs.
"U.S. Appl. No. 12/249,454, Final Office Action mailed Nov. 23, 2011", 8 pgs.
"U.S. Appl. No. 12/249,454, Non Final Office Action mailed Apr. 6, 2011", 8 pgs.
"U.S. Appl. No. 12/249,454, Response filed Aug. 30, 2011 to Non Final Office Action mailed Apr. 6, 2011", 14 pgs.
"U.S. Appl. No. 12/249,479, Final Office Action mailed Dec. 2, 2011", 8 pgs.
"U.S. Appl. No. 12/249,479, Non Final Office Action mailed Apr. 5, 2011", 10 pgs.
"U.S. Appl. No. 12/249,479, Response filed Apr. 2, 2012 to Final Office Action mailed Dec. 2, 2011", 9 pgs.
"U.S. Appl. No. 12/249,479, Response filed Aug. 30, 2011 to Non Final Office Action mailed Apr. 5, 2011", 12 pgs.
"U.S. Appl. No. 12/249,508, Notice of Allowance mailed Feb. 14, 2012", 7 pgs.
"U.S. Appl. No. 12/249,508, Notice of Allowance mailed Oct. 5, 2011", 9 pgs.
"U.S. Appl. No. 12/249,508, Response filed Aug. 30, 2011 to Restriction Requirement mailed Jun. 30, 2011", 8 pgs.
"U.S. Appl. No. 12/249,508, Restriction Requirement mailed Jun. 30, 2011", 6 pgs.
"U.S. Appl. No. 12/412,608, Final Office Action mailed Nov. 21, 2011", 6 pgs.
"U.S. Appl. No. 12/412,608, Non Final Office Action mailed May 26, 2011", 8 pgs.
"U.S. Appl. No. 12/412,608, Notice of Allowance mailed Jun. 6, 2012", 7 pgs.
"U.S. Appl. No. 12/412,608, Response filed Apr. 18, 2012 to Final Office Action mailed Nov. 21, 2011", 7 pgs.
"U.S. Appl. No. 12/412,608, Response filed Sep. 26, 2011 to Non Final Office Action mailed May 26, 2011", 9 pgs.
"U.S. Appl. No. 13/094,416, Response filed Sep. 17, 2012 to Restriction Requirement mailed Aug. 16, 2012", 8 pgs.
"U.S. Appl. No. 60/947,308 Application filed Jun. 29, 2007", 47 pgs.
"ATROSTIM Phrenic Nerve Stimulator", Product Brochure, AtroTech Oy, P.O. Box 28, FIN-33712 Tampere, Finland, (Jun. 2004), 2 pgs.
"Australian Application Serial No. 2005319498, First Examiner Report mailed May 27, 2010", 3 pgs.
"Australian Application Serial No. 2005319498, Response filed Feb. 21, 2011 to First Examiner Report mailed May 27, 2010", 11 pgs.
"Coating Process for Composite Implants", Medical Materials Update, vol. 1, No. 12, (Jan. 1995), 3 pgs.
"European Application Serial No. 05849548.2, Communication and Supplementary Partial European Search Report mailed Feb. 29, 2008", 8 pgs.

(56) References Cited

OTHER PUBLICATIONS

"European Application Serial No. 05849548.2, Communication mailed Jun. 9, 2009", 3 pgs.
"European Application Serial No. 0584548.2, Office Action mailed Dec. 20, 2010", 4 pgs.
"European Application Serial No. 05849548.2, Response filed Jun. 29, 2011 to Non Final Office Action mailed Dec. 20, 2010", 9 pgs.
"European Application Serial No. 05849548.2, Response filed Dec. 16, 2009 to Communication mailed Jun. 9, 2009", 10 pgs.
"European Application Serial No. 08772198.1, Office Action mailed Sep. 13, 2010", 6 pgs.
"European Application Serial No. 08772198.1, Response filed Mar. 31, 2011 to Communication mailed Sep. 30, 2010", 11 pgs.
"European Application Serial No. 08781107.1, Invitation Pursuant to Rule 63(1) EPC mailed Jul. 13, 2010", 3 pgs.
"European Application Serial No. 08781107.1, Communication dated Feb. 9, 2010", 2 pgs.
"European Application Serial No. 08781107.1, Extended European Search Report mailed Nov. 25, 2010", 6 pgs.
"European Application Serial No. 08781107.1, Response filed Mar. 5, 2010 to Communication dated Feb. 9, 2010", 2 pgs.
"European Application Serial No. 08781107.1, Response filed Jun. 14, 2011 to Communication mailed Dec. 14, 2010", 10 pgs.
"European Application Serial No. 08781107.1, Response filed Sep. 22, 2010 to the Invitation to Rule 63(1)", 11 pgs.
"European Application Serial No. 08796045.6, European Search Report mailed Sep. 21, 2010", 6 pgs.
"European Application Serial No. 08796045.6, Office Action mailed Jan. 4, 2012", 4 pgs.
"European Application Serial No. 08796045.6, Response filed Apr. 14, 2011 to Communication dated Oct. 8, 2010", 10 pgs.
"Implant Attaches to Bone by Chemical Bond", Medical Materials Update, vol. 4, No. 7, (Aug. 1997), 2 pgs.
"International Application Serial No. PCT/US05/45044, International Search Report mailed May 2, 2006", 1 pg.
"International Application Serial No. PCT/US08/68627, International Search Report mailed Sep. 10, 2008", 1 pg.
"International Application Serial No. PCT/US08/68627, Written Opinion mailed Sep. 10, 2008", 4 pgs.
"International Application Serial No. PCT/US08/68632, International Search Report mailed Sep. 11, 2008", 2 pgs.
"International Application Serial No. PCT/US08/68632, Written Opinion mailed Sep. 11, 2008", 4 pgs.
"International Application Serial No. PCT/US08/68654, International Search Report mailed Sep. 22, 2008", 2 pgs.
"International Application Serial No. PCT/US08/68654, Written Opinion mailed Sep. 22, 2008", 4 pgs.
"International Application Serial No. PCT/US2005/045044, Written Opinion mailed May 2, 2006", 3 pgs.
"International Application Serial No. PCT/US2008/068618, International Search Report mailed Nov. 26, 2008", 2 pgs.
"International Application Serial No. PCT/US2008/068618, Written Opinion mailed Nov. 26, 2008", 6 pgs.
"International Application Serial No. PCT/US2008/068630, International Search Report mailed Sep. 10, 2008", 1 pg.
"International Application Serial No. PCT/US2008/068630, Written Opinion mailed Sep. 10, 2008", 4 pgs.
"International Application Serial No. PCT/US2008/068635, International Search Report mailed Sep. 9, 2008", 3 pgs.
"International Application Serial No. PCT/US2008/068635, Written Opinion mailed Sep. 9, 2008", 4 pgs.
"International Application Serial No. PCT/US2008/068647, International Search Report mailed Sep. 22, 2008", 2 pgs.
"International Application Serial No. PCT/US2008/068647, Written Opinion mailed Sep. 22, 2008", 4 pgs.
"International Application Serial No. PCT/US2009/060293, International Preliminary Report on Patentability mailed Apr. 12, 2011", 10 pgs.
"International Application Serial No. PCT/US2009/060293, International Search Report mailed Mar. 10, 2010", 6 pgs.

"International Application Serial No. PCT/US2009/060293, Invitation to Pay Additional Fee mailed Dec. 18, 2009", 5 pgs.
"International Application Serial No. PCT/US2009/060293, Written Opinion mailed Mar. 10, 2010", 10 pgs.
"International Application Serial No. PCT/US2009/068859, International Search Report mailed Jul. 5, 2010", 7 pgs.
"International Application Serial No. PCT/US2009/068859, Invitation to Pay Additional Fee mailed Apr. 15, 2010", 6 pgs.
"International Application Serial No. PCT/US2009/068859, Written Opinion mailed Jul. 5, 2010", 12 pgs.
"International Application Serial No. PCT/US2011/033944, International Search Report mailed Sep. 8, 2011", 5 pgs.
"International Application Serial No. PCT/US2011/033944, Written Opinion mailed Sep. 8, 2011", 9 pgs.
"Japanese Application Serial No. 2007-548389, Final Office Action dated Aug. 2, 2011"(w/ English Translation), 5 pgs.
"Japanese Application Serial No. 2007-548289, Office Action mailed Mar. 6, 2012", (w/ English Translation), 3 pgs.
"Japanese Application Serial No. 2007-548289, Office Action mailed Nov. 24, 2010", (w/ English Translation), 7 pgs.
"Japanese Application Serial No. 2007-548289, Response filed May 20, 2011 to Office Action mailed Nov. 24, 2010", (w/ English Translation of Amended Claims), 9 pgs.
"Japanese Application Serial No. 2007-548289, Response filed Oct. 26, 2011 to Office Action mailed Aug. 3, 2011", (w/ English Translation of Amended Claims), 10 pgs.
"Victrex's PEEK Used for Dialysis Machines", Medical Material's Update, vol. 3, No. 3, (Apr. 1996), pp. 1-2.
Alboni, P., "Bundle Branch Blocks Anatomically Located in The His Bundle", Italian Cardiology Journal, 10(12), (w/English Translation thereof, followed by Italian publication), (1980), 1583-1587.
Al-Khadra, A., et al., "The Role of Electroporation in Defibrillation", Circulation Research, 87(9), (Oct. 2000), 797-804.
Avitall, B., et al., "Iontophoretic Transmyocardial Drug Delivery. A Novel Approach to Antiarrhythmic Drug Therapy", Circulation, 85(4), (1992), 1582-1593.
Barba-Pichardo, Rafael, et al., "Permanent His-Bundle Pacing in Patients With Infra-Hisian Atrioventricular Block", Rev Esp Cardiol. 59(6), (Mar. 9, 2006), 553-558.
Barton, A. J., et al., "Bacterial Adhesion to Orthopedic Implant Polymers", J. Biomed. Mat. Res., 30(3), (Mar. 1996), 403-410.
Bonanno, C., et al., "Effect on QRS Duration and Feasibility of Septal and Multisite Right Ventricular Pacing", Cardiostimolazione, 14(3), (Abstract Only), (Sep. 1996), p. 195.
Buckingham, Thomas A., et al., "Acute Hemodynamic Effects of Atrioventricular Pacing at Differing Sites in the Right Ventricle Individually and Simultaneously", PACE, 20[Pt. I], (Apr. 1997), 909-915.
Cantu, F., et al., "Validation of Criteria for Selective His Bundle and Para-Hisian Permanent Pacing", PACE, vol. 29, (Dec. 2006), 1326-1333.
Cantu, Francesco, et al., "A Methodical Approach to Validate Selective His Bundle and para-Hisian Permanent Pacing", [abstract] Oasis, (2006), 1 pg.
Catanzariti, Domenico, et al., "Permanent His Bundle Pacing Does Not Induce Ventricular Dyssonchrony. An Echocardiographic Intrapatient Study of Comparison With Conventional Pacing", [abstract] Oasis, (2006), 1 pg.
Chiu, L., et al., "Method for One-Click Deployment and or Configuration of Real-Time Software System Modifications", U.S. Appl. No. 60/558,921, filed Apr. 2, 2004, 8 pgs.
Chudzik, Michal, "Ventricular Endocardial Right Bifocal Stimulation in Treatment of Severe Dilated Cardiomyopathy Heart Failure in Patients with Unsuccessful Biventricular Pacemaker Implantation", [abstract CP07] Europace Supplements, vol. 7, (May 2005), 1 pg.
Deshmukh, P., et al., "Permanent, Direct His-Bundle Pacing: A Novel Approach to Cardiac Pacing in Patients With Normal His-Purkinje Activation", Circulation, 101(8), (Feb. 29, 2000), 869-877.
Deshmukh, Pramod M., et al., "Direct His-Bundle Pacing: Present and Future", PACE, vol. 27, Part II, (Jun. 2004), 862-870.
Dong, Y., et al., "His-Bundle Capture Verification and Monitoring", U.S. Appl. No. 61/328,248, filed Apr. 27, 2010, 40 pgs.

(56) References Cited

OTHER PUBLICATIONS

El-Sherif, N., et al., "Normalization of Bundle Branch Block Patterns by Distal His Bundle Pacing: Clinical and Experimental Evidence of Longitudinal Dissociation in the Pathologic His Bundle", Circulation, 57(3), (Mar. 1978), 473-483.
Flynn, David M, et al., "Extendable and Retractable Lead Having a Snap-Fit Terminal Connector", U.S. Appl. No. 11/173,664, filed Jul. 1, 2005, 53 pgs.
Furman, S., et al., "Chapter 5—Permanent Pacemaker Implementation", A Practice of Cardiac Pacing, Futura Publishing Co., Inc. Mount Kisco, NY, (1986), 97-127.
Genc, S., et al., "Methodology for Locking Feature Selection in Integral Snap-Fit Assembly", Proceedings of DETC '97, 1997 ASME Engineering Technical Conferences, (Sep. 1997), 1-11.
Golia, P., et al., "Multisite Pacing of Right Ventricle in Heart Failure: Echocardiographic Evaluation", [Abstract] Cardiostimolazione, vol. 14, Num. 3, (Sep. 1996), 5 pgs.
Grosfeld, M. J.W., et al., "Testing a New Mechanism for Left Interventricular Septal Pacing: The Transseptal Route", Europace, vol. 4, (Oct. 2002), 439-444.
Ha, S. W., et al., "Plasma-Sprayed Hydroxylapatite Coating on Carbon Fibre Reinforced Thermoplastic Composite Materials", J. Mater. Sci. Mater. Med., vol. 5, No. 6-7, (1994), pp. 481-484.
Hummel, J. D., et al., "Augmentation of Cardiac Output by Anodal Pacing", [Abstract] Circulation, 90(No. 4, Part 2), (Oct. 1994), pg. 1-69.
Ingle, Frank, et al., "Lead Motion Sensing Via Cable Mcrophonics", U.S. Appl. No. 61/359,430, filed Jun. 29, 2010, 52 pgs.
Jockisch, K. A., et al., "Biological Response to Chopped-Carbon-Fiber-Reinforced Peek", J. Biomed. Mater. Res., vol. 26, No. 2, (1992), pp. 133-146.
Kanno, S., et al., "Establishment of a simple and practical procedure applicable to therapeutic angiogenesis", Circulation, 99(20), (May 25, 1999), 2682-2687.
Kavanagh, K. M., et al., "Monophasic Versus Biphasic Cardiac Stimulation: Mechanism of Decreased Energy Requirements", PACE, vol. 13, No. 10, (Oct. 1990), 10 pgs.
Kaye, D. M., et al., "Frequency-dependent activation of a constitutive nitric oxide synthase and regulation of contractile function in adult rat ventricular myocytes", Circulation Research, 78(2), (Feb. 1996), 217-24.
Knapp, C. P, et al., "Snap Fit Terminal Connector", U.S. Appl. No. 09/184,226, filed Nov. 2, 1998, 39 pgs.
Kutarski, A., et al., "Factors Influencing Differences of RVA & RVOT Pacing Hemodynamic Effects", [abstract CP05] Europace Supplements, vol. 7, (May 2005), p. 288.
Kutarski, A., et al., "Right Ventricular Outflow Tract and Dual Site Right Ventricular Pacing—The Comparison With Apex Pacing", [abstract CP08] Europace Supplements, vol. 7, (May 2005), p. 288.
Labhasetwar, V., et al., "Iontophoresis for Modulation of Cardiac Drug Delivery in Dogs", Proc. Natl. Acad.Sci. USA, 92(7), (Mar. 28, 1995), 2612-2616.
Lazarus, A., et al., "Reduction in Energy Pacing Thresholds by Overlapping Biphasic Stimulation Versus Conventional Bipolar Pacing", PACE, vol. 21, (Nov. 1998), 6 pgs.
Lin, T. W., et al., "Glass Peek Composite Promotes Proliferation and Osteocalcin of Human Osteoblastic Cells", J. Biomed. Mater. Res., vol. 36, No. 2, (1997), pp. 137-144.
Lupi, G., et al., "Effects of Right Ventricular Pacing on Intra-Left Ventricular Electromechanical Activation in Patients with Native Narrow QRS.", American Journal of Cardiology, vol. 98, (2006), 219-222.
Macnair, R., et al., "The Response of Primary Rat and Human Osteoblasts and an Immortalized Rat Osteoblast Cell Line to Orthopaedic Materials: Comparative Sensitivity of Several Toxicity Indices", J. Mater. Sci. Mater. Med., vol. 8, No. 2, (1997), pp. 105-111.
Manolis, Antonis S., "The Deleterious Consequences of Right Ventricular Apical Pacing: Time to Seek Alternate Site Pacing", PACE, vol. 29, (Mar. 2006), 298-315.
Mansourati, J., et al., "Left ventricular-based pacing in patients with chronic heart failure: comparison of acute hemodynamic benefits according to underlying heart disease", Eur J Heart Fail., 2(2), (Jun. 2000), 195-9.
Meyer, M. R., et al., "Long-Term Durability of the Interface in FRP Composites After Exposure to Simulated Physiologic Saline Environments", J. Biomed. Mater. Res., 28(10), (1994), 1221-1231.
Mond, Harry G., et al., "The Right Ventricular Outflow Tract: The Road to Septal Pacing", PACE, vol. 30, (Apr. 2007), 482-491.
Morina-Vazquez, Pablo, et al., "Cardiac Resynchronization Through Selective His Bundle Pacing in a Patient with the So-Called InfraHis Atrioventricular Block", PACE, vol. 28, (Jul. 2005), 726-729.
Morrison, C., et al., "In Vitro Biocompatibility Testing of Polymers for Orthopaedic Implants Using Cultured Fibroblasts and Osteoblasts", Biamaterials, vol. 16, No. 13, (1995), 987-992.
Narula, O. S, "Longitudinal dissociation in the His bundle. Bundle branch block due to asynchronous conduction within the His bundle in man", Circulation, 56(6), (Dec. 1977), 996-1006.
Occhetta, E., et al., "Prevention of Ventricular Desynchronization by Permanent Para-Hisian Pacing After Atrioventricular Node Ablation in Chronic Atrial Fibrillation: A Crossover, Blinded, Randomized Study Versus Apical Right Ventricular Pacing", Journal of the American College of Cardiology, 47(10), (May 16, 2006), 1938-1945.
Padeletti, Luigi, et al., "Physiologic Pacing: New Modalities and Pacing Sites", PACE, vol. 29, Supplement 2, (Dec. 2006), S73-S77.
Pastore, G., et al., "Different Degree of Ventricular Dyssyncrony Induced by Right Apical, Hissian and Para Hissian Ventricular Pacing", [abstract] Oasis, (2006), 1 pg.
Pastore, Gianni, et al., "Direct His-Bundle Pacing Preserves the Normal Left Activation Sequence: An Acute Echocardiographic Study", [abstract] Oasis, (2006), 1 pg.
Puech, P., et al., "Narrowing and normalization of QRS stimulation of the His bundle in complete left bundle branch block.", Scholarly Journal of the French Cardiology Society, vol. 72, No. 8, (w/ English Translation thereof, followed by French publication), (Aug. 1979), 815-824.
Qu, J, et al., "HCN2 overexpression in newborn and adult ventricular myocytes: distinct effects on gating and excitability", Circ. Res., vol. 89(1), (Jul. 6, 2001), e8-14.
Qu, J, et al., "Sympathetic innervation alters activations of pacemaker current (If) in rat ventricle", J. Physiol, 526 Pt 3, (Aug. 1, 2000), 561-569.
Ravazzi, A., et al., "Improvement of Interventricular Activation Time Using Biphasic Pacing Pulses at Different Sites on Right Ventricle Septal Wall", Progress in Biomedical Research, 4(3), (Jun. 1999), 248-253.
Reddy, G. S., "Bundle of His Stimulation System", U.S. Appl. No. 61/045,168, filed Apr. 15, 2008, 37 pgs.
Saksena, S., et al., "Chapter 9—Pacemaker Implantation Techniques", Electrical Therapy for Cardiac Arrhythmias, W.B. Saunders Co., Philadelphia, PA, (1990), pp. 173, 181-183.
Scheinman, M. M., et al., "Long-Term His-Bundle Pacing and Cardiac Function", Circulation, 101(8), (2000), 836-837.
Schoenfeld, M. H., "Alternative Site Pacing to Promote Cardiac Synchrony: Has Conventional Pacing Become Unconventional?", Journal of the American College of Cardiology, 47(10), (2006), 1946-1948.
Shi, W, et al., "Distribution and prevalence of hyperpolarization-activated cation channel (HCN) mRNA expression in cardiac tissues", Circ. Res., vol. 85(1), (Jul. 9, 1999), e1-6.
Sotobata, I., et al., "Population distribution of Frank-vectorcardiographic measurements of Healthy Japanese men", Japanese Circulation Journal, 38(8), (1975), 895-903.
Soyer, J., et al., "Experimental Characterisation of a Carbon/Peek Hip Prothesis in Fatigue", Chirurgie, 121, (1996), p. 658-663.
Sweeney, M. O., et al., "Adverse Effect of Ventricular Pacing on Heart Failure and Atrial Fibrillation Among Patients with Normal Baseline QRS Duration in a Clinical Trial of Pacemaker Therapy for Sinus Node Dysfunction", Circulation, 107(23), (2003), 2932-2937.
Sweeney, M. O., et al., "Heart Failure During Cardiac Pacing", Circulation, 113(17), (2006), 2082-2088.

(56) References Cited

OTHER PUBLICATIONS

Takatsuki, et al., "Clinical Implications of "pure" Hisian pacing in addition to para-Hisian pacing for the diagnosis of supraventricular tachycardia", Heart Rhythm 3 (12), (Dec. 2006), 1412-1418.
Tanabe, M., et al., "Biventricular Pacing Worsened Dyssynchrony in Heart Failure Patient with Right-Bundle Branch Block", International Journal of Cardiology, 138(3), (available online Aug. 15, 2008 / epub doi:10.10161.ijcard.2008.06.063 ), (2010), e47-e50.
Thakral, A, et al., "Effects of anodal vs. cathodal pacing on the mechanical performance of the isolated rabbit heart", J. Appl Physiol., 89(3), (Sep. 2000), 1159-64.
Tse, Hung-Fat, et al., "Selection of Permanent Ventricular Pacing Site: How Far Should We Go?", Journal of the American College of Cardiology, 48(8), (Sep. 26, 2006), 1649-1651.
Van Gelder, B. M., et al., "Hemodynamic Effect of RV Apex vs RV Septum Pacing in a Monoventricular and Biventricular Configuration in Patients with Heart Failure", [abstract CP06] Europace Supplements, vol. 7, (May 2005), p. 288.
Victor, F., et al., "A Randomized Comparison of Permanent Septal Versus Apical Right Ventricular Pacing: Short-Term Results", Journal of Cardiovascular Electrophysiology, 17(3), (Mar. 2006), 238-242.
Wang, S. C.-J., et al., "Improved Method and System for Managing Voice Prompt Recordings Prior to Deployment", U.S. Appl. No. 60/532,271, filed Dec. 23, 2003, 12 pgs.
Wenz, L. M., et al., "In Vitro Biocompatibility of Polyetheretherketone and Polysulfone Composites", J. Biomed. Mater. Res., vol. 26, No. 2, (1990), pp. 207-215.
Winckels, S. K. G., et al., "High-Septal Pacing Reduces Ventricular Electrical Remodeling and Proarrhythmia in Chronic Atrioventricular Block Dogs", Journal of the American College of Cardiology, 50(9), (Aug. 28, 2007), 906-913.
Yu, H., et al., "MinK-related peptide 1: A beta subunit for the HCN ion channel subunit family enhances expression and speeds activation", Circ. Res., 88(12), (Jun. 22, 2001), e84-7.
Zanon, F., et al., "A Feasible Approach for Direct His-Bundle Pacing Using a New Steerable Catheter to Facilitate Precise Lead Placement", Journal of Cardiovascular Electrophysiology, 17(1), (Jan. 2006), 29-33.
Zanon, Francesco, et al., "A New Technique for Direct His-Bundle Pacing: Acute and Mid-Term Electrical Data Results", [abstract] Oasis, (2006), 1 pg.
Zanon, Francesco, et al., "Direct His Bundle Pacing Preserves Coronary Perfusion Compared With Right Ventricular Apical Pacing: A Prospective, Cross-Over Mid-Term Study", Europace, vol. 10, (2008), 580-587.
Zhang, Y., et al., "His Electrogram Alternans Reveal Dual-Wavefront Inputs Into and Longitudinal Dissociation Within the Bundle of His", Circulation, 104(7), (2001), 832-838.
Zhu, Q., et al., "Methods, Devices and Systems for Cardiac Pacing Therapies Using Intrinsic Activity", U.S. Appl. No. 61/139,117, filed Dec. 19, 2008, 22 pgs.
"U.S. Appl. No. 11/300,242, Notice of Allowance mailed May 8, 2012", 6 pgs.
"U.S. Appl. No. 11/300,242, Notice of Allowance rnailed Aug. 24, 2012", 7 pgs.
"U.S. Appl. No. 12/147,317, Notice of Allowance mailed Jul. 2, 2012", 7 pgs.
"U.S. Appl. No. 12/147,376, Notice of Allowance mailed Aug. 30, 2012", 7 pgs.
"U.S. Appl. No. 12/147,376, Notice of Allowance mailed Dec. 7, 2012", 7 pgs.
"U.S. Appl. No. 12/249,454, Non Final Office Action mailed Sep. 4, 2012", 8 pgs.
"U.S. Appl. No. 12/249,454, Notice of Allowance mailed Dec. 26, 2012", 5 pgs.
"U.S. Appl. No. 12/249,454, Response filed Apr. 2, 2012 to Final Office Action mailed Nov. 23, 2011", 12 pgs.
"U.S. Appl. No. 12/249,454, Response filed Dec. 4, 2012 to Non Final Office Action mailed Sep. 4, 2012", 12 pgs.
"U.S. Appl. No. 12/249,479, Non Final Office Action mailed Sep. 4, 2012", 7 pgs.
"U.S. Appl. No. 12/249,479, Notice of Allowance mailed Jan. 8, 2013", 5 pgs.
"U.S. Appl. No. 12/249,479, Response filed Dec. 4, 2012 to Non Final Office Action mailed Sep. 4, 2012", 9 pgs.
"U.S. Appl. No. 12/249,508, Notice of Allowance mailed Jun. 12, 2012", 7 pgs.
"U.S. Appl. No. 13/094,416, Non Final Office Action mailed Dec. 14, 2012", 13 pgs.
"U.S. Appl. No. 13/094,416, Notice of Allowance mailed Jun. 25, 2013", 8 pgs.
"U.S. Appl. No. 13/094,416, Response filed Apr. 15, 2013 to Non Final Office Action mailed Dec. 14, 2012", 14 pgs.
"U.S. Appl. No. 13/094,416, Restriction Requirement mailed Aug. 16, 2012", 5 pgs.
"U.S. Appl. No. 13/139,951, Final Office Action mailed Aug. 23, 2013", 6 pgs.
"U.S. Appl. No. 13/139,951, Non Final Office Action mailed May 16, 2013", 6 pgs.
"U.S. Appl. No. 13/139,951, Notice of Allowance mailed Nov. 8, 2013", 9 pgs.
"U.S. Appl. No. 13/139,951, Response filed Aug. 14, 2013 to Non Final Office Action mailed May 16, 2013", 16 pgs.
"U.S. Appl. No. 13/139,951, Response filed Oct. 23, 2013 to Final Office Action mailed Aug. 23, 2013", 11 pgs.
"U.S. Appl. No. 13/211,937, Non Final Office Action mailed Jan. 15, 2013", 7 pgs.
"U.S. Appl. No. 13/211,937, Notice of Allowance mailed May 13, 2013", 6 pgs.
"U.S. Appl. No. 13/211,937, PTO Response to 312 Amendment mailed Aug. 20, 2013", 2 pgs.
"U.S. Appl. No. 13/211,937, Response filed Apr. 11, 2013 to Non Final Office Action mailed Jan. 15, 2013", 8 pgs.
"U.S. Appl. No. 13/216,969, Non Final Office Action mailed Dec. 18, 2013", 12 pgs.
"U.S. Appl. No. 13/217,776, Non Final Office Action mailed Jan. 15, 2013", 6 pgs.
"U.S. Appl. No. 13/217,776, Notice of Allowance mailed May 15, 2013", 6 pgs.
"U.S. Appl. No. 13/217,776, Response filed Apr. 11, 2013 to Non Final Office Action mailed Jan. 15, 2013", 9 pgs.
"U.S. Appl. No. 13/223,919, Non Final Office Action mailed Oct. 29, 2013", 11 pgs.
"U.S. Appl. No. 13/282,163, Non Final Office Action mailed Oct. 28, 2013", 12 pgs.
"U.S. Appl. No. 13/404,814, Examiner Interview Summary mailed Dec. 17, 2013", 3 pgs.
"U.S. Appl. No. 13/404,814, Final Office Action mailed Nov. 21, 2013", 11 pgs.
"U.S. Appl. No. 13/404,814, Non Final Office Action mailed Jul. 16, 2013", 9 pgs.
"U.S. Appl. No. 13/404,814, Notice of Allowance mailed Feb. 12, 2014", 7 pgs.
"U.S. Appl. No. 13/404,814, Response filed Jan. 21, 2014 to Final Office Action mailed Nov. 21, 2013".
"U.S. Appl. No. 13/404,814, Response filed Oct. 16, 2013 to Non Final Office Action mailed Jul. 16, 2013", 13 pgs.
"U.S. Appl. No. 13/688,859, Final Office Action mailed Oct. 8, 2013", 5 pgs.
"U.S. Appl. No. 13/688,859, Non Final Office Action mailed Jun. 20, 2013", 6 pgs.
"U.S. Appl. No. 13/688,859, Notice of Allowance mailed Jan. 27, 2014", 6 pgs.
"U.S. Appl. No. 13/688,859, Response filed Jan. 8, 2014 to Final Office Action mailed Oct. 8, 2013", 7 pgs.
"U.S. Appl. No. 13/688,859, Response filed Sep. 20, 2013 to Non Final Office Action mailed Jun. 20, 2013", 12 pgs.
"U.S. Appl. No. 13/875,681, Non Final Office Action mailed Oct. 17, 2013", 5 pgs.
"U.S. Appl. No. 13/875,681, Response filed Jan. 16, 2014 to Non Final Office Action mailed Oct. 17, 2013", 9 pgs.
"U.S. Appl. No. 60/947,310, Application filed Jun. 29, 2007", 49 pgs.

(56) References Cited

OTHER PUBLICATIONS

"Australian Application Serial No. 2009327369, First Examination Report mailed Jul. 19, 2012", 3 pgs.
"European Application Serial No. 05849548.2, Office Action mailed Jan. 16, 2013", 3 pgs.
"European Application Serial No. 08772198.1, Examination Notification Art 94(3) mailed Nov. 27, 2013", 3 pgs.
"European Application Serial No. 08796045.6, Response filed May 14, 2012 to Office Action mailed Jan. 4, 2012", 8 pgs.
"International Application Serial No. PCT/US2011/033944, International Preliminary Report on Patentability mailed Nov. 8, 2012", 9 pgs.
"International Application Serial No. PCT/US2012/026571, International Preliminary Report on Patentability mailed Sep. 26, 2013", 9 pgs.
"International Application Serial No. PCT/US2012/026571, International Search Report mailed Oct. 18, 2012", 4 pgs.
"International Application Serial No. PCT/US2012/026571, Written Opinion mailed Oct. 18, 2012", 7 pgs.
"Japanese Application No. 2010-515189, Response Apr. 19, 2013 to Non Final Office Action dated Feb. 12, 2013", With English Claims, 7 pgs.
"Japanese Application No. 2010-515198, Non Final Office Action dated Jul. 2, 2013", With English Translation, 14.
"Japanese Application Serial No. 2007-548289, Office Action mailed Nov. 6, 2012", With English Translation, 3 pgs.
"Japanese Application Serial No. 2007-548289, Response filed Feb. 14, 2013 to Office Action mailed Nov. 6, 2012", With English Claims, 7 pgs.
"Japanese Application Serial No. 2007-548289, Response filed Jun. 4, 2012 to Office Action mailed Mar. 6, 2012", With English Translation, 4 pgs.
"Japanese Application Serial No. 2010-515189, Non-Final Office Action dated Jul. 2, 2013", With English Translation, 6.
"Japanese Application Serial No. 2010-515189, Office Action mailed Feb. 12, 2013", With English Translation, 9 pgs.
"Japanese Application Serial No. 2010-515196, Office Action mailed Jan. 15, 2013", With English Translation, 8 pgs.
"Japanese Application Serial No. 2010-515196, Office Action mailed Sep. 3, 2013", With English Translation, 10 pgs.
"Japanese Application Serial No. 2010-515198, Examiners Decision of Final Refusal mailed Nov. 26, 2013", With English Translation, 5 pgs.
"Japanese Application Serial No. 2010-515198, Office Action mailed Feb. 12, 2013", With English Translation, 16 pgs.
"Japanese Application Serial No. 2010-515198, Response filed Apr. 24, 2013 to Office Action mailed Feb. 12, 2013", With English Claims, 7 pgs.
"Japanese Application Serial No. 2011-531237, Office Action mailed Jan. 15, 2013", With English Translation, 7 pgs.
"Japanese Application Serial No. 2011-542513, Office Action mailed Jan. 15, 2013", With English translation, 6 pgs.
"Japanese Application Serial No. 2011-542513, Response filed Apr. 12, 2013 to Non Final Office Action dated Apr. 12, 2013", With English Claims, 10.
Arcot-Krishnamurthy, S., et al., "Timing for His-Bundle Pacing", U.S. Appl. No. 13/277,617, filed Oct. 20, 2011, 40 pgs.
Wang, et al., "System for Managing Voice Files of a Voice Prompt Server", U.S. Appl. No. 10/835,444, filed Apr. 28, 2004.
U.S. Appl. No. 13/875,681, filed May 2, 2013, Apparatus for Treating the Physiological Electric Conduction of the Heart.
U.S. Appl. No. 13/223,919, filed Sep. 1, 2011, Systems, Devices and Methods Relating to Endocardial Pacing or Resynchronization.
U.S. Appl. No. 13/688,859, filed Nov. 29, 2012, Devices and Methods for Steering Electrical Stimulation in Cardiac Rhythm Management.
U.S. Appl. No. 14/027,568, filed Sep. 16, 2013, Systems, Devices and Methods for Monitoring Efficiency of Pacing.
U.S. Appl. No. 13/282,163, filed Oct. 26, 2011, Circuit-Based Devices and Methods for Pulse Control of Endocardial Pacing in Cardiac Rhythm Management.
U.S. Appl. No. 14/029,588, filed Sep. 17, 2013, Endocardial Pacing Devices and Methods Useful for Resynchronization and Defibrillation.
U.S. Appl. No. 13/216,969, filed Aug. 24, 2011, Endocardial Pacing Relating to Conduction Abnormalities.
U.S. Appl. No. 13/862,776, filed Apr. 15, 2013, Methods, Devices and Systems for Cardiac Rhythm Management Using an Electrode Arrangement.
U.S. Appl. No. 13/650,444, filed Oct. 12, 2012, Methods, Devices and Systems for Single-Chamber Pacing Using a Dual-Chamber Pacing Device.
U.S. Appl. No. 13/139,951, filed Jan. 6, 2012, Devices, Methods, and Systems Including Cardiac Pacing.
U.S. Appl. No. 13/404,814, filed Feb. 24, 2012, His Capture Verification Using Electro-Mechanical Delay.

\* cited by examiner

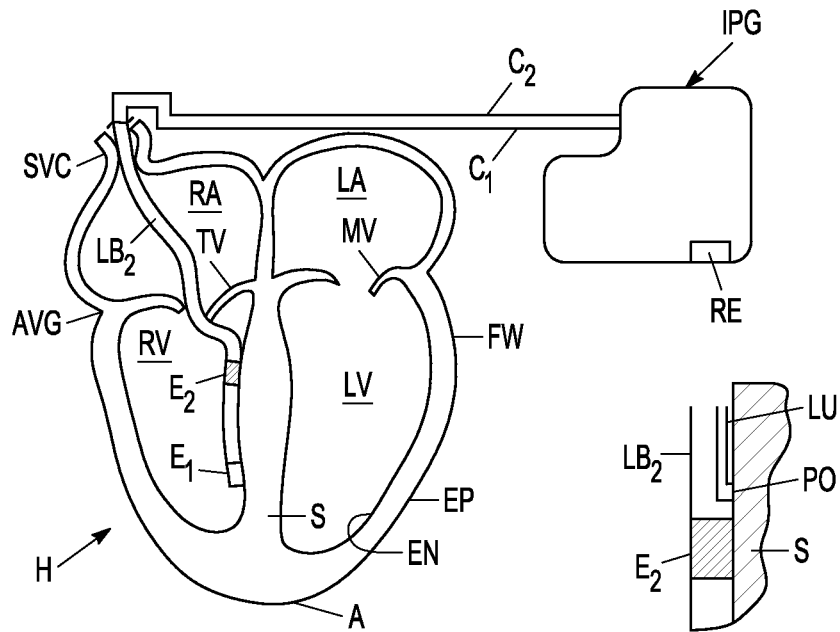
*FIG. 2*
*FIG. 2A*
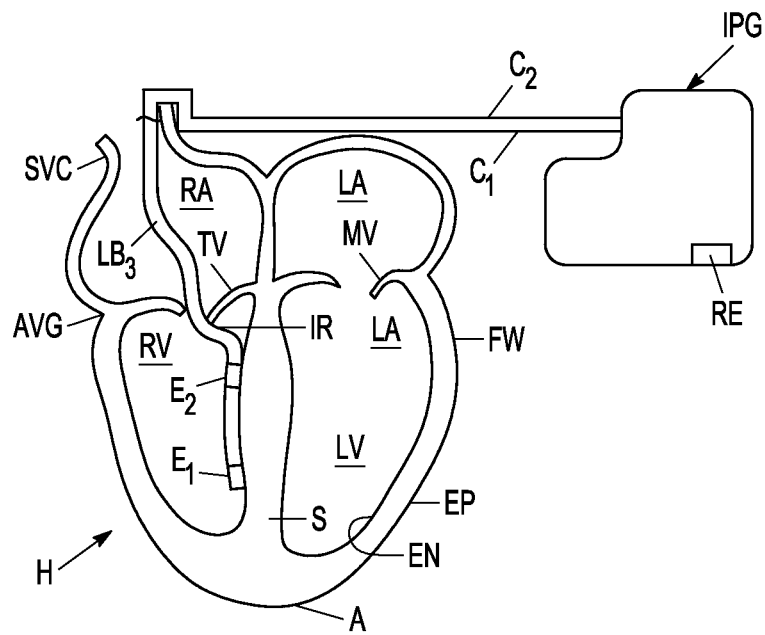
*FIG. 3*

VENTRICULAR PACING

CLAIM OF PRIORITY

This patent document is a continuation under 35 U.S.C. §120 of U.S. patent application Ser. No. 12/412,608 filed on Mar. 27, 2009, now U.S. Pat. No. 8,285,376, which is continuation under 35 U.S.C. §120 of U.S. patent application Ser. No. 11/300,611 filed on Dec. 13, 2005 (U.S. Pat. No. 7,512, 440), which claims foreign priority to Argentina Patent Application No. 20040104782 filed on Dec. 20, 2004 by inventors Daniel Felipe Ortega and Alberto German Giniger and entitled "A New Pacemaker Which Reestablishes Or Keeps The Physiological Electric Conduction Of The Heart And A Method Of Application."

FIELD AND BACKGROUND

This invention pertains to ventricular pacing. More particularly, this invention pertains to synchronous pacing of a patient's left ventricle by electrodes residing in the patient's right ventricle.

Percutaneously placed pacing electrodes are commonly positioned only in the right-side chambers (right atrium or right ventricle) of the heart. Access to such chambers is readily available. Such access is through the superior vena cavity into the right atrium and then into the right ventricle.

Electrode placement into the left ventricle is normally avoided. Access is not as direct as in right ventricle placement. More important, emboli risk in the left ventricle is greater than in the right ventricle. Emboli which might develop in the left ventricle by reason of the electrode placement have direct access to the brain via the aorta from the left ventricle. This presents a significant risk of stroke.

Historically, pacing electrodes were placed only in the right ventricle to treat bradycardia (slow heart rate). Right atrium pacing was less understood and was more complex.

With advances in electro-physiology, pacing of both the right atrium and right ventricle was developed. Such dual chamber pacing resulted in better hemodynamic output than right ventricle-only pacing.

In addition to treating bradycardia, dual chamber pacing maintained synchrony between the chambers. Recent clinical evidence suggests that conventional ventricular pacing from the right ventricle creates asynchronous contraction of the left ventricle, leading to inefficient mechanical contraction and reduced hemodynamic performance. Long term right ventricular pacing has even been found to be associated with an increased risk of developing or worsening heart failure.

At first, combined pacing of the right ventricle and right atrium was performed by advancing two electrode leads through the superior vena cava into the right atrium. The first of these terminated at one or more electrodes which were attached to the endocardium of the atrium. The second lead (also having one or more electrodes) was advanced into the right ventricle with the electrode attached to the endocardium of the right ventricle.

Such historical dual chamber pacing was not without complications. The use of two leads resulting in a doubling of volume of the vasculature (e.g., the superior vena cava and jugular vein) occupied by such leads. Further, attachment of an electrode to the atrial wall was unreliable.

The historical problems of the dual chamber pacing led to the development of so-called "single pass" leads. Such leads have both the atrial and ventricle electrodes on a common lead.

Beginning in the 1990's, cardiac pacing has been considered for treatment of congestive heart failure (CHF). CHF patients suffer from low left ventricular output.

CHF is an extremely serious and progressive disease. While drug treatments exist, they may delay but do not stop or reverse the disease.

CHF patients face a progression of a debilitating condition which drastically alters lifestyle and will ultimately be fatal in the absence of heart transplant. Unfortunately, many patients do not qualify for such transplants and the available number of donor hearts is inadequate to treat those who do qualify.

Many CHF patients have low left ventricular output due to a mismatch between contractile forces produced by muscles of the left ventricle free wall (the external wall of the left ventricle) and the opposing septum (the wall dividing the right and left ventricles). Ideally, the free wall and septum contract in synchrony during systole to urge blood through the aortic valve. When out of synchrony, the septal wall may be contracting while the free wall is relaxed. Instead of urging blood flow, at least a portion of the contractile energy of the septum is wasted.

The mismatch of free wall and septal contractility is believed to be due to disorders in the electrical conduction systems of the heart. This conduction system includes the A-V node, the Bundle of His and the Purkinje fibers.

Located at the upper end of the septum, the sinus node creates the synchronized neuraly-mediated signal for cardiac pacing. These signals are conducted by the specialized fibers comprising the A-V node and the Bundle of His (extending along the length of the septum) and further conducted to the muscle of the heart through the Purkinje fibers. The Purkinje fibers originate in the septum and extend through the apex of the heart and to the exterior walls of the heart including into and up the free wall of the left ventricle.

In a healthy heart, the signal flow from the A-V node to the free wall of the left ventricle is rapid to insure the free wall and septum contract in synchrony. For example, a stimulating signal may flow to the free wall in about 70-90 milli-seconds. In patients with conduction abnormalities, this timing may be significantly delayed (to 150 milli-seconds or more) resulting in asynchronous contraction.

In some patients, the conduction path through the Purkinje fibers may be blocked. The location of the block may be highly localized (as in the case of so-called "left bundle branch block" or LBBB) or may include an enlarged area of dysfunctional tissue (which can result from infarction). In such cases, all or a portion of the free wall of the left ventricle is flaccid while the septum is contracting. In addition to contributing to asynchronous contraction, the contraction force of the free wall is weakened.

To address asynchronous contraction, CHF patients can be treated with cardiac pacing of the left ventricle. Such pacing includes applying a stimulus to the septal muscles in synchrony with stimulation applied to the muscles of the free wall of the left ventricle. While infracted tissue will not respond to such stimulus, non-infarcted tissue will contract thereby heightening the output of the left ventricle.

The prior art has developed various techniques for accomplishing left ventricle stimulation. For reasons noted above (i.e., emboli formation), endocardially positioned electrodes in the left ventricle are avoided. However, electrodes can be placed on the epicardial surface of the heart through surgical placement. The epicardial electrodes are positioned on the free wall of the left ventricle and are paced in synchrony with electrodes placed near the septum in the right ventricle.

Since epicardial electrodes require a surgical placement, the patient is subjected to two procedures—percutaneous placement of right ventricle electrodes (normally performed in a catheter lab by an electrophysiologist) and surgical placement of epicardial electrodes on the left ventricle (normally placed by a cardiac surgeon in a surgical suite). Also, such dual procedure is a burden on medical resources.

Percutaneous procedures have been developed for placement of an electrode to stimulate the free wall of the left ventricle. In such a procedure, an electrode lead is advanced through the coronary sinus. Part of the venous system, the coronary sinus extends from the right atrium and wraps around the heart on or near the epicardial surface and partially overlies the left ventricle free wall. In this percutaneous procedure, the electrode remains positioned in the coronary sinus overlying the left ventricle free wall with the lead passing through the coronary sinus and through the right atrium to the implantable pulse generator.

Unfortunately, a coronary sinus electrode is frequently less than optimal. The portion of the free wall most directly influenced by the electrode is the tissue directly underlying the coronary sinus at the location of the electrode. For many patients, this may not be the location of the free wall most in need of a stimulating therapy. Accordingly, the resulting therapy is sub-optimal. Also, some patients may have an extremely small diameter coronary sinus or the coronary sinus may have such a tortuous shape that percutaneous positioning of an electrode within the coronary sinus is impossible or very difficult. Not uncommonly, advancing a lead from the right atrium into the coronary sinus is extremely time-consuming. Even if successful, such a procedure consumes significant health care resources (including precious catheter lab time). Finally, there are now up to three leads passing through and occupying the space of the superior vena cava (i.e., leads for the electrodes in the right ventricle, right atrium and the coronary sinus). U.S. patent application Publ. No. 2005/0125041 published Jun. 9, 2005 shows (in FIG. 1) three leads passed through a superior vena cava with one lead residing in the right atrium, one in the right ventricle and one passed through the coronary sinus to overly the left ventricle.

SUMMARY

As will be described with reference to a preferred embodiment, aspects of the present invention are directed to a cardiac pacing system and method. As will be described, these aspects include electrodes in the right ventricle near the septal wall. These electrodes create a pulsed electrical field which stimulates both the septum and at least a portion of the free wall of the left ventricle.

According to a specific example embodiment of the present invention, a method and apparatus are disclosed for treating a condition of a patient's heart. The method includes placing a first electrode and a second electrode in a right ventricle of the heart. A reference electrode may be used, e.g., placed within the patient and internal or external to the heart. A pacing signal is generated including a first signal component and a second signal component to provide energy at levels relative to a reference level, with the first and second signal components having opposite polarity and with both of the first and second components having a potential relative to the reference level. The pacing signal and the placement of the electrodes are selected to alter a contraction of a left ventricle of the heart as further characterized in the examples hereinafter.

The above summary is limited to characterizing certain aspects and is not intended to describe each illustrated embodiment or every implementation of the present invention. The figures and detailed description that follow, including that described in the appended claims, more particularly exemplify these embodiments.

BRIEF DESCRIPTION OF THE DRAWINGS

The invention may be more completely understood in consideration of the detailed description of various embodiments of the invention that follows in connection with the accompanying drawings as follows:

FIG. 2 is the view of FIG. 1 showing electrodes in contact with a septal wall;

FIG. 2A is a cross-sectional view of an electrode lead showing a mechanism for attachment of an electrode to a septal wall;

FIG. 3 is the view of FIG. 1 showing an electrode lead formed, in part, from shape memory alloys for urging electrodes against a septal wall;

DETAILED DESCRIPTION

Referring now to the various drawing figures, a description of the preferred embodiment of the present invention will now be provided. Incorporated herein by reference are the disclosures of U.S. Pat. No. 6,230,061 B1 to Hartung issued May 8, 2001 and U.S. Pat. No. 6,907,285 to Denker, et al., dated Jun. 14, 2004; U.S. patent application Publ. No. 2004/0153127 published Aug. 5, 2004; U.S. Pat. No. 6,643,546 B2 to Mathis et al. dated Nov. 4, 2003.

Generally speaking, the present invention is directed to creating a pulsed electrical field in the right ventricle with the field stimulating the musculature of the septum and free wall of the left ventricle to create coordinated contraction of the septum and free wall.

Figure 1:
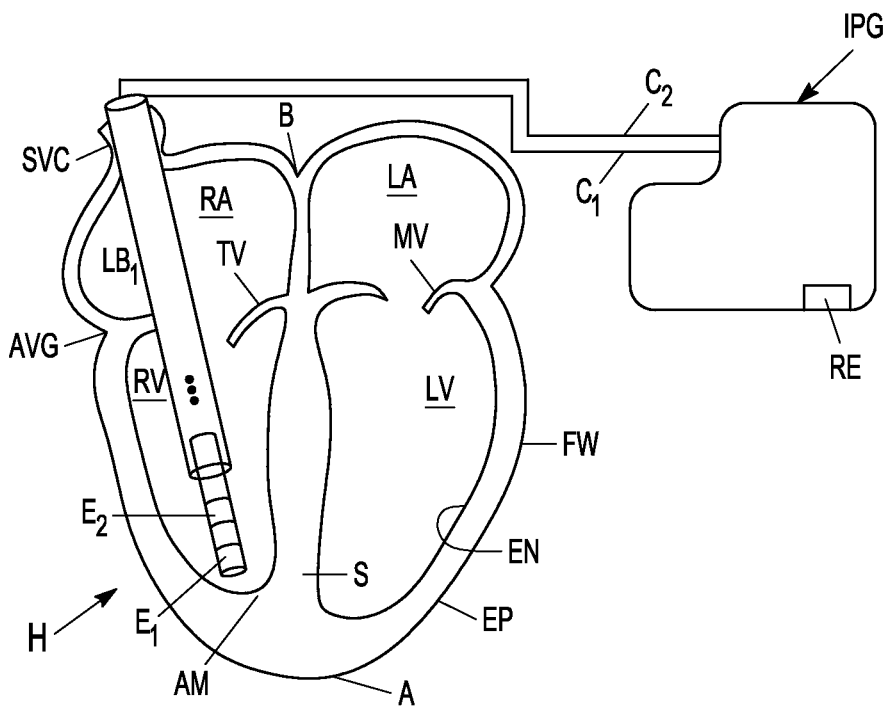
FIG. 1 is a schematic cross sectional view of the heart showing relevant anatomical features and schematically showing a catheter with pacing electrodes in the right ventricle and a subcutaneously placed implantable pulse generator.

The present invention can be practiced with currently commercially available electrode leads and can also be enhanced with novel leads. FIG. 1 illustrates the invention in practice with such commercially available lead. As is the conventional usage for referencing relative direction, the terms "left" and "right" are used herein with reference to the patient's perspective. The terms "upper" and "lower" and similar terms such as "up" or "down" are used with reference to the base B of the heart being high and the apex A of the heart H being a lower end.

In FIG. 1, a patient's heart H is schematically shown in cross-section. The heart H includes the upper chambers of the right atrium RA and left atrium LA. The lower chambers are the right ventricle RV and left ventricle LV. Of the various venous vessels opening into the right atrium RA, only the superior vena cava SVC is shown. Also, of the various heart valves, only the mitral valve MV (separating the left atrium LA from the left ventricle LV) and the tricuspid valve TV (separating the right atrium RA from the right ventricle RV) are shown. The septum S separates the right and left ventricles RV, LV and the free wall FW of the left ventricle LV is separately labeled. The surface of the heart wall tissue opposing the chambers is the endocardium and is labeled as EN. The exterior surface of the heart is the epicardium and is labeled EP. Not shown are coronary vessels of the heart or the pericardium surrounding the heart H.

In FIG. 1, an electrode lead is shown having a lead body $LB_1$ and exposed electrodes $E_1$ and $E_2$. The first electrode $E_1$ is positioned near the distal tip of the lead body $LB_1$. The second electrode $E_2$ is positioned more proximally on the lead body $LB_1$. At the distal end, an attachment mechanism AM (such as a passive fixation design with tines or an active fixation design with a metallic helix) is shown for securing the first electrode $E_1$ to the musculature of the heart H. The spacing of electrodes $E_1$, $E_2$ could be greater than that of convention pacing electrodes permitting positioning of the first electrode $E_1$ at the apex of the right ventricle RV and the second electrode $E_2$ in the right ventricle RV near the tricuspid valve TV. However, conventional leads with convention spacing have been used with the first or distal electrode attached to the septum (e.g., by a helix attachment HA) as shown in FIG. 7A.

The lead body $LB_1$ is flexible and includes a bio-compatible, electrically insulating coating surrounding first and second conductors $C_1$, $C_2$ separately connected to the first and second electrodes $E_1$, $E_2$. In the various Figures, the lead bodies are broken at a line at the SVC to reveal the internal conductors $C_1$, $C_2$ extending to an implantable pulse generator IPG. In fact, the conductors $C_1$, $C_2$ are contained within the material of the lead body $LB_1$ along their length. The term "implantable pulse generator IPG" is intended to include pacemakers, implantable converter defibrillators (ICD) and cardia resynchronization therapies (CRT), all known in the art.

The proximal end of the lead body terminates at a pin connector (not shown) as is customary. The pin connector has exposed electrical contacts uniquely connected to each of the conductors $C_1$, $C_2$. The pin connector may be releasably connected to the pulse generator IPG with the exposed contacts making electrical connection with unique contacts of the circuitry of the pulse generator IPG.

It will be appreciated that the prior art contains numerous examples of cardiac leads for placement in a chamber of the heart where the leads have, as described above, two or more electrodes spaced along a length of the lead, attachment mechanisms such as passive or active fixation and conductors and connector pins as described. The current invention is not limited to pacing leads only, but rather is equally deployable with prior art ICD leads where it is customary to contain at least two electrodes in the RV. Such leads are selected of biocompatible material and treated (such as sterilized) for chronic placement in the patient.

The implantable pulse generator IPG is a small metallic container sealed for implantation in the patient and protecting internal circuitry. Commonly, such pulse generators are placed subcutaneously (e.g., in a dissected space between the skin and muscle layers of the patient). For cardiac pacing, such pulse generators are positioned in the upper chest on either the left or right front side of the patient near a shoulder. However, placement need not be so restricted and such pulse generators could be placed in any convenient location selected by the physician.

Pulse generators contain internal circuitry for creating electrical impulses which are applied to the electrodes after the lead is connected to the pulse generator. Also, such circuitry may include sensing and amplification circuitry so that electrodes $E_1$, $E_2$ may be used as sensing electrodes to sense and have the IPG report on the patient's electrophysiology.

The lead may be introduced to the vasculature through a small incision and advanced through the vasculature and into the right atrium RA and right ventricle to the position shown in FIG. 1. Such advancement typically occurs in an electrophysiology lab where the advancement of the lead can be visualized through fluoroscopy.

The pulse generator contains a battery as a power supply. With subcutaneous placement, replacement of a battery is well-known procedure. However, improvements in battery designs have resulted in longer-lasting batteries with the benefit of reducing the frequency of battery replacement. Alternatively, such batteries may be rechargeable in situ as is known in the art.

The pulse generator circuitry controls the parameters of the signals coupled to the electrodes $E_1$, $E_2$. These parameters can include pulse amplitude, timing, pulse duration by way of example. The internal circuitry further includes circuit logic permitting reprogramming of the pulse generator to permit a physician to alter pacing parameters to suit the need of a particular patient. Such programming can be affected by inputting programming instructions to the pulse generator via wireless transmission from an external programmer. Pulse generators commonly include an exposed contact on the exterior of the generator housing. Such pulse generators may also be partially covered with an insulator such as silicone with a window formed in the silicone to expose a portion of the metallic housing which functions as a return electrode in so-called unipolar pacing. In conventional bipolar pacing, the window is not necessary. Most commonly, the electrode is connected by the circuitry of the housing to an electrical ground. It will be appreciated that pulse generators as thus described are well known in the art and form no part of this invention per se.

While an implantable pulse generator is described in a preferred embodiment, the pulse generator may be external and coupled to the electrodes by percutaneous leads or wireless transmission. For example, a control of an implanted electrode is known for phrenic nerve stimulation and is described more fully in a product brochure "ATROSTIM PHRENIC NERVE STIMULATOR", AtroTech Oy, P.O. Box 28, FIN-33721, Tampere, Finland (June 2004). The Atrostim device sends signals from an external controller to an implanted antenna.

External pacing devices are typically used for providing temporary pacing therapy. The current invention is also believed to have advantages for this application as critically-ill patients requiring emergency, temporary pacing may also suffer further from asynchronous cardiac contraction associated with conventional RV pacing. If desired, an external unit can be used to test a patient's suitability for the treatment. Patient's who benefit from the therapy can then receive an implantable pulse generator for longer-term use.

Figure 8:
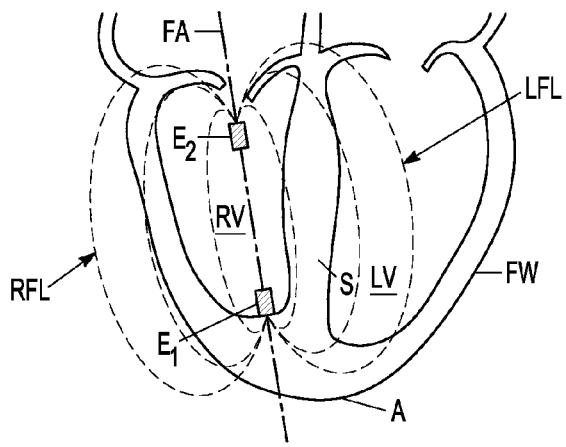
FIG. 8 is a view, taken in cross-section, of right and left ventricles of a heart showing the electrodes of FIG. 1 (without showing the lead body) energized to create electromagnetic fields.

FIGS. 1 and 8 illustrate commercially available leads and the associated electrical fields with both electrodes residing within the right ventricle with the distal electrode secured to the apex of the right ventricle. In FIG. 8, only the ventricles RV, LV are shown for ease of illustration. Also, for ease of illustration, FIG. 8 shows only the electrodes $E_1$, $E_2$ without showing the remainder of the lead body $LB_1$.

While conventional bipolar leads are acceptable for use with the present invention, a wider spacing between electrodes $E_1$, $E_2$ can increase the field but can sacrifice some sensing capability. This trade-off can be mitigated by use of a three-electrode lead in the right ventricle RV. Such a lead would have a tip electrode and two ring electrodes, one located near the tip in the RV apex and one in the high part of the atrium, near the tricuspid valve. The sensing is performed between the tip and closer electrode. This will provide good so-called "near field" sensing and avoid so-called "far field" sensing of the atrium or skeletal muscle activity. The pacing could be between the ring electrodes to the return electrode located distally to the heart (as will be described). One could also combine the tip and nearest ring as one electrode to the return electrode and the other ring electrode to the return electrode at the opposite polarity.

Figure 18:
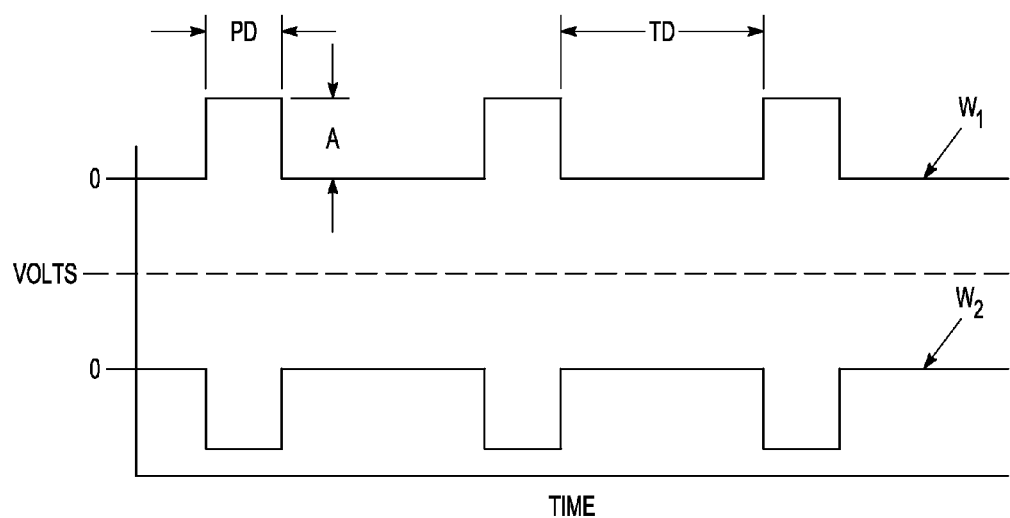
FIG. 18 is a graphical representation of pulsed waveforms to be applied by first and second electrodes of the various embodiments.

The pulse generator IPG generates a first and a second pulsed waveform $W_1$, $W_2$ applied, respectively, to the first and second electrodes $E_1$, $E_2$. FIG. 18 shows such waveforms $W_1$, $W_2$. By way of example, and not intended to be limiting, the pulse duration PD is between about 0.1 to 2.0 milliseconds, the amplitude A may be 0.1 Volts to 10 or 20 Volts and the time delay TD between pulses is a targeting heart rate (e.g., 50 to 200 beats per minutes).

In FIG. 18, the pulses are shown as square waveforms but, in practice, can be any geometry. The first electrode $E_1$ has positive charged pulses only. The second electrode $E_2$ has negative charged pulses timed to coincide with the positive charged pulses of the positive electrode $E_1$. While direct current (DC) pulses are preferred, the electrodes $E_1$, $E_2$ could be energized with alternating current pulses with the signals to the electrodes $E_1$, $E_2$ out of phase such that the positive pulses on the first electrode $E_1$ coincide with negative pulses on the second electrode $E_2$ and negative pulses on the first electrode $E_1$ coincide with positive pulses on the second electrode $E_2$.

With the electrodes $E_1$, $E_2$ charged with opposite pulses, it is Applicants' current understanding that an electrical field is created between the electrodes $E_1$, $E_2$ with a field axis FA (FIG. 8) extending in a line between the electrodes $E_1$, $E_2$. In the absence of distorting influences (such as external magnetic fields, external electrodes or non-homogonous conductivity due to variances in conductivity of blood, tissue bone, etc.), the field is symmetrical about the field axis FA and is represented by field lines illustrated in the drawings as left field lines LFL to the left of the axis FA (with left being from the patient's perspective) and right field lines RFL. The field lines represent the intensity of the electrical field. The intensity diminishes rapidly as a function of the distance from the field axis FA.

In the embodiment of FIG. 1, in order for the fields generated by the electrodes $E_1$, $E_2$ to have a significant influence on both the septal walls and the free wall FW of the left ventricle LV, a voltage potential across the electrodes must be substantially high. However, such high voltages are not practical in a pacing electrode and are more normally associated with defibrillating treatments. Also, such voltages would cause an extremely significant drain on a battery requiring an impractical frequency of battery replacement.

Figure 9:
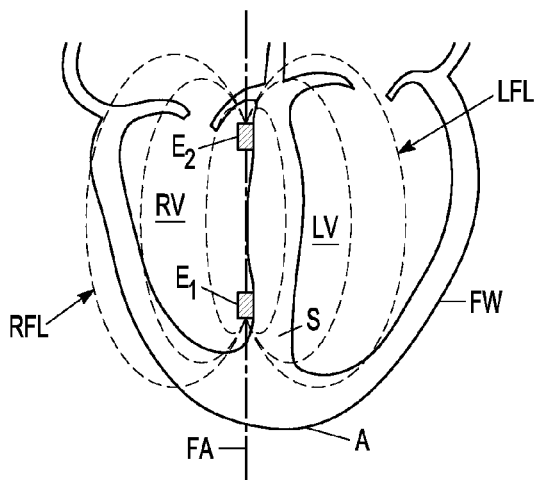
FIG. 9 is the view of FIG. 8 showing the field shifted toward the left ventricle in response to repositioning of leads.

FIG. 9 illustrates benefits associated with movement of the electrodes $E_1$, $E_2$ from the interior of the right ventricle RV (FIGS. 1 and 8) to direct placement of the electrodes $E_1$, $E_2$ on the septal wall S. Such movement shifts the field lines toward both the septal wall S and the free wall FW of the left ventricle LV. However, it is believed that even with such improvement, voltages required for effective stimulation of the septal wall and the free wall of the left ventricle would be impractically high.

Figure 10:
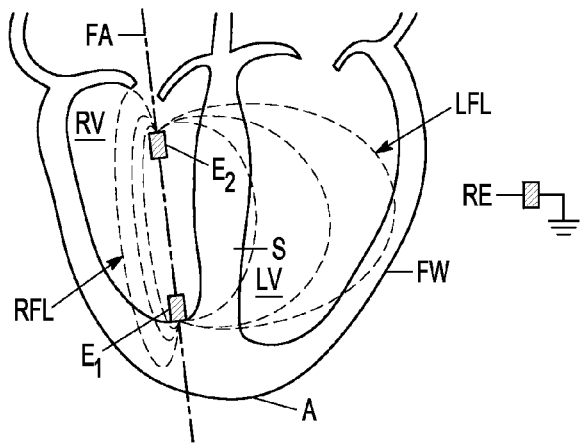
FIG. 10 is the view of FIG. 8 showing the field distorted toward a free wall of the left ventricle by influence of an external reference electrode.

The present invention utilizes a reference electrode RE in combination with the electrodes $E_1$, $E_2$ in the right ventricle to result in effective pacing of the left ventricle LV. Although the physics and physiology of the mechanism of action are not fully understood, it is presently believed that the reference electrode RE distorts the electromagnetic field otherwise created between the right ventricle electrodes $E_1$, $E_2$ to urge an intensity of the electromagnetic field deeper into the septal wall S of the left ventricle LV. It is believed this occurs by creating a third high current density spot (or spots) away from the two electrodes in the wall and towards the reference electrode at the point where the current flows between the electrode E1 and the reference electrode RE and between the electrode E2 and the reference electrode RE coincide in space and time. This is illustrated in FIG. 10. Such a phenomenon is believed to facilitate the activation of the surviving conduction fibers in the Left Bundle Branch Block (LBBB) patients and Purkinje fibers and create a more rapid and uniform activation of the left ventricle LV that follows a similar pattern to the normal activation present in patients without LBBB.

The reference electrode may be physically attached to the housing of the implantable pulse generator IPG (and thereby having a neutral charge). Such an electrode RE is shown in FIGS. 1-7B. It will be appreciated that the reference electrode RE can be connected to the implantable pulse generator IPG by a conductor. The reference electrode could be another common electrode that exists in the conventional pacing or ICD system, such as an electrode in the atrium or a defibrillation coil electrode situated in the SVC, RA or RV.

As shown in FIG. 10, the consequence of the reference electrode RE is presently believed to have a deforming effect on the electromagnetic field generated between the first and second electrodes $E_1$, $E_2$. This is illustrated in FIG. 10 by distorting the left field lines LFL toward the septal wall S and free wall FW of the left ventricle LV. Also, the right field lined RFL are compressed toward the axis FA to alter the field from the symmetric presentation of FIGS. 8 and 9 to the asymmetric presentation of FIG. 10 with the field biased toward the septal wall S and the free wall FW of the left ventricle LV.

It has been found that within energy levels associated with available implantable pulse generators (up to 10 or 20 volts) effective activation of the left ventricle LV can be achieved with the pacing arrangement of FIG. 7A, where the first electrode $E_1$ is attached to the mid- or upper-septum. In such arrangement, the reference electrode RE is on the housing of the generator IPG and positioned subcutaneously near the right or left shoulder. The re-direction of the field as described, the inventors believe, may also be useful in decreasing defibrillation thresholds if arrangement similar to FIG. 7B is used. In FIG. 7B large segmented (for flexibility) electrodes E2, E3 are shown in the superior vena cava SVC near the atrium RA and in the right ventricle to serve as shocking electrodes to defibrillate a patient.

Figure 14:
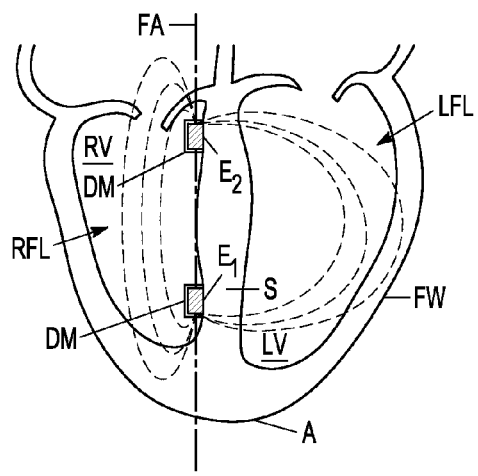
FIG. 14 is the view of FIG. 9 with fields distorted to be biased toward the left ventricle by the addition of dielectric material on a side of the electrodes of FIG. 9.

FIG. 14 illustrates how the field can also be distorted by dielectric material DM placed on a side of the electrodes $E_1$, $E_2$ opposite the septal wall S. The dielectric material DM result in a distortion of the electrical field biasing the left field lines LFL toward the septal wall S and the free wall FW. Of course, this configuration will work even better with a reference electrode which will enhance the benefit.

While positioning of the electrodes $E_1$, $E_2$ within the volume of the right ventricle RV is effective in combination with a reference electrode RE (FIG. 10), movement of the electrodes $E_1$, $E_2$ directly against the septal wall S may further enhance the therapeutic benefit of the present invention for reasons described above. Various techniques for movement of the electrodes $E_1$, $E_2$ against the septal wall S are disclosed.

FIG. 2 illustrates a lead body $LB_2$ in the right ventricle RV with the electrodes $E_1$, $E_2$ directly placed on the septal wall S and held in place against the septal wall through any suitable means. For example, FIG. 2A illustrates one embodiment for attachment of an electrode against the septal wall. The lead body $LB_2$ is shown has having an internal lumen LU with a port PO near an electrode (e.g., electrode $E_2$). Any suitable attachment mechanism (such as a pigtail guidewire or an injected bio-adhesive) can be passed through the lumen LU and port PO to fix the electrode $E_2$ in abutment against the septal wall S. Further, a guide catheter could also be used in moving the implantable lead to assist in the mapping of the optimal location of the septum. The optimal lead location can be determined with the assistance of the surface ECG parameters (e.g. QRS width and/or activation vectors).

FIG. 3 illustrates the electrodes $E_1$, $E_2$ against the septal wall S but without requiring an attachment mechanism. Instead, an intermediate region IR of the lead body $LB_3$ is formed of shaped memory material (such as nitinol) to assume an S-shaped configuration and urge the electrodes $E_1$, $E_2$ against the septal wall S.

Figure 4:
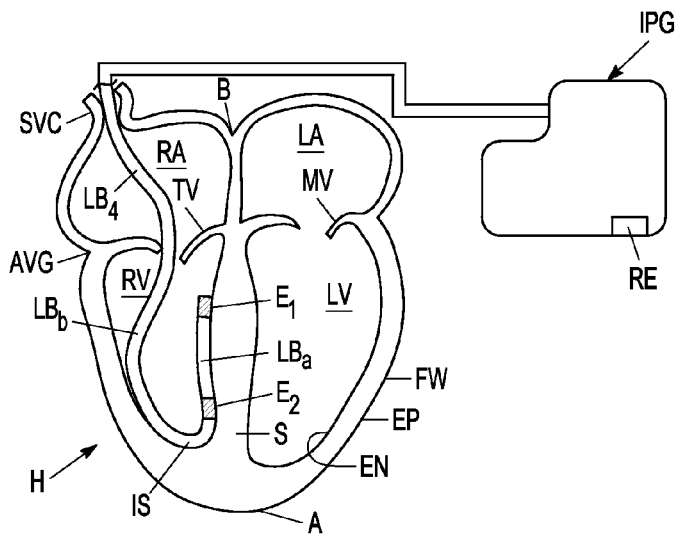
FIG. 4 is the view of FIG. 1 showing a further embodiment of an electrode lead for urging electrodes against a septal wall.

In FIG. 4, the lead body $LB_4$ has two components $LB_a$, $LB_b$ joined by an intermediate section IS which may be formed of any elastomeric material (such as a shaped memory material). The intermediate section IS is biased to urge the two components $LB_a$, $LB_b$ into collinear alignment. With the intermediate section IS placed against the apex of the right ventricle RV, the bias of the intermediate section IS urges the electrodes $E_1$, $E_2$ against the septal wall S.

Figure 5:
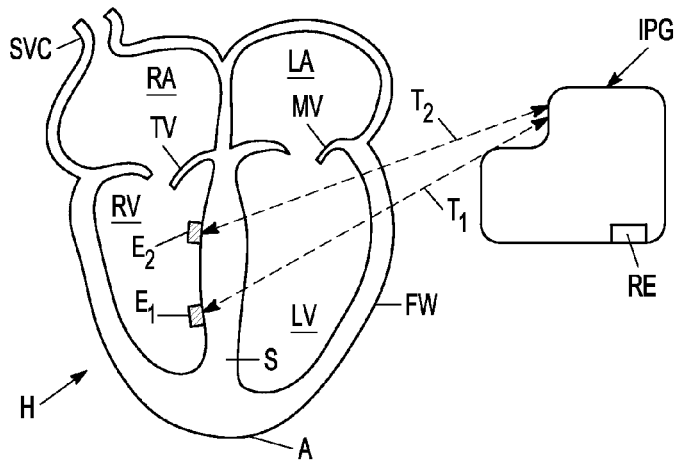
FIG. 5 is the view of FIG. 1 showing electrodes on a septal wall and energized by wireless transmission.
Figure 6:
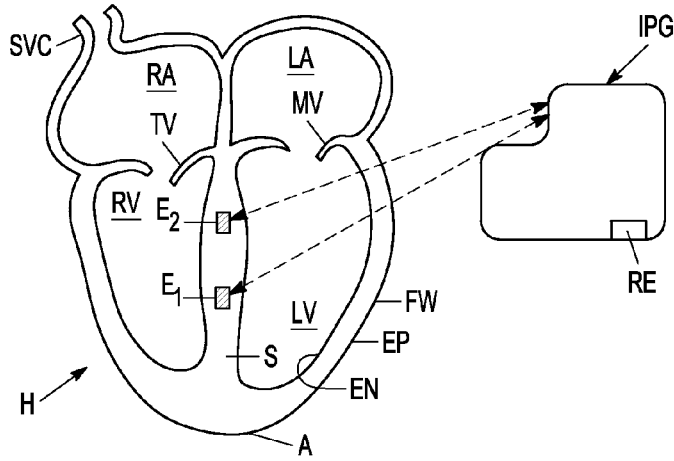
FIG. 6 is the view of FIG. 5 showing electrodes embedded within the septal wall.

FIG. 5 illustrates the electrodes $E_1$, $E_2$ individually placed on the septal wall S and not retained on a lead body. In such an embodiment, the electrodes $E_1$, $E_2$ may be energized in a pacing waveform by wireless transmission signals $T_1$, $T_2$ from the implantable pulse generator IPG. Wireless transmission from a controller to an electrode is shown in U.S. Pat. No. 6,907,285 to Denker, et al., dated Jun. 14, 2004. Alternatively, the electrodes $E_1$, $E_2$ may be directly imbedded as microstimulators into the tissue of the septal wall S as illustrated in FIG. 6. Microstimulators for implantation into human tissue are shown in U.S. patent application Publ. No. 2004/0153127 published Aug. 5, 2004.

Figure 11:
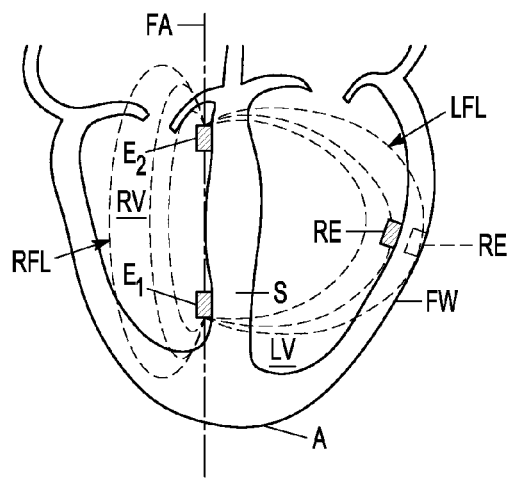
FIG. 11 is the view of FIG. 9 with a reference electrode placed within the left ventricle.
Figure 12:
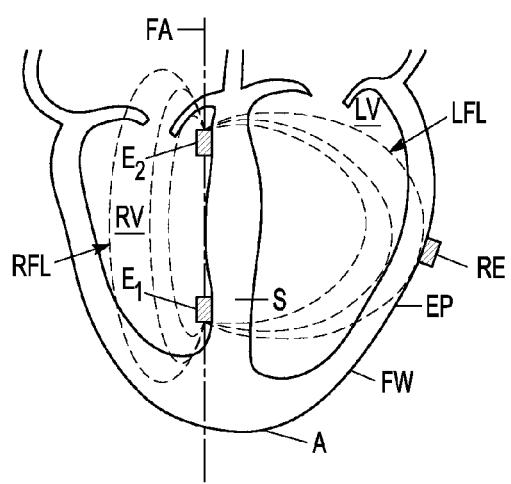
FIG. 12 is the view of FIG. 14 with an external electrode placed on the epicardial surface of the heart.
Figure 13:
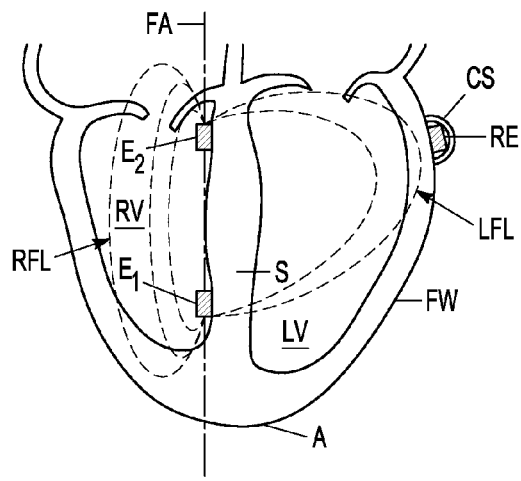
FIG. 13 is a view with an external electrode placed within a coronary sinus.

The positioning of the reference electrode RE may be directly on the housing of the implantable pulse generator IPG or may be separate from the internal pulse generator as previously mentioned. While not preferred, the reference electrode RE can be placed in the left ventricle (FIG. 11) (or in the tissue of the free wall FW as shown in phantom lines in FIG. 11), on the epicardial surface (FIG. 12) or in the coronary sinus CS (FIG. 13).

Positioning the reference electrode RE relative to the heart can affect the distortion of the field in the area of the left ventricle free wall FW subject to pacing. Particularly for a subcutaneously placed reference electrode (which is preferred to minimize the invasive nature of the procedure), the electrical conduction path from the right ventricle RV to the reference electrode will vary considerably between patients.

Figure 15:
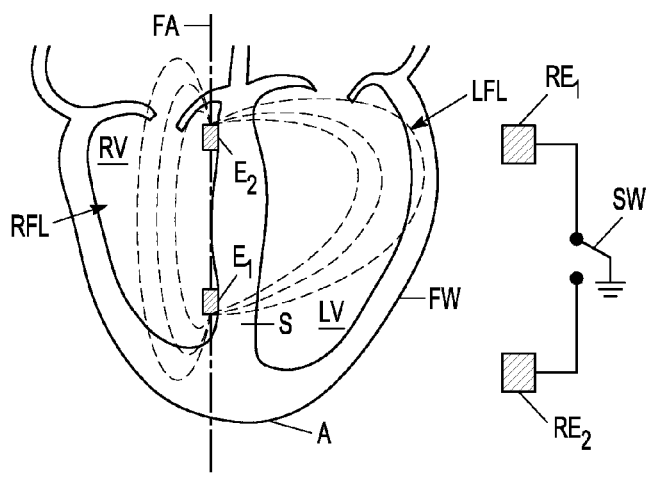
FIG. 15 shows a field distorted towards an upper end of the free wall in response to a reference electrode in a first position.
Figure 16:
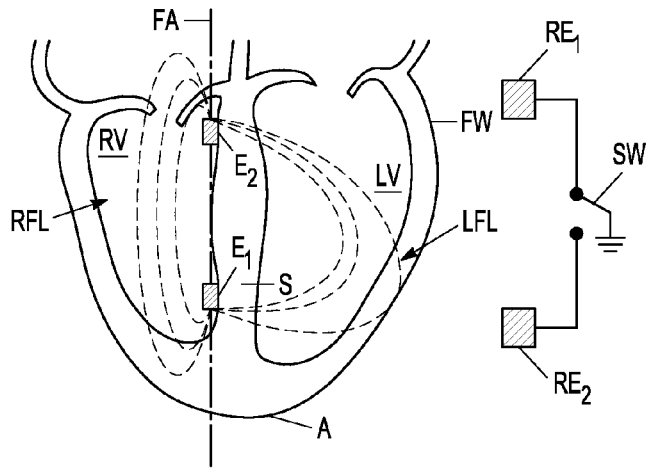
FIG. 16 is the view of FIG. 15 with a reference electrode switched to a second position.

Also, the direction of field distortion may alter the region of the left ventricle LV subject to pacing. For example, FIG. 15 illustrates the reference electrode $RE_1$ placed high relative to the heart resulting in a distortion of the field toward the upper end of the left ventricle septum and free wall FW. FIG. 16 illustrates placement of a reference electrode $RE_2$ lower relative to the heart and to deflect the intensity of the field toward the lower end of the left ventricle septum and free wall FW.

While the reference electrode could be a single electrode, multiple electrodes could be provided for subcutaneous placement and each connected by a switch circuitry SW of the implantable pulse generator as illustrated in FIGS. 15 and 16. The patient's response can be noted with each of the several reference electrodes $RE_1$, $RE_2$ separately connected to the ground or housing of the implantable pulse generator. The patient can then be treated with the electrode showing the most effectiveness for the particular patient. Further, over time, a patient's response may change and the implantable pulse generator can be reprogrammed to select any one of the other reference electrodes as the switched electrode.

Figure 7:
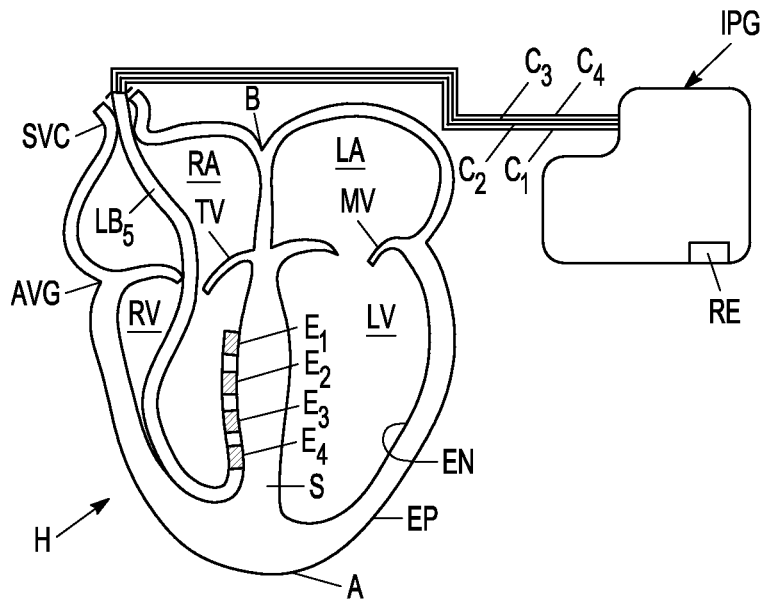
FIG. 7 is the view of FIG. 4 showing the lead of FIG. 4 with multiple electrodes urged against the septal wall.
Figure 7A:
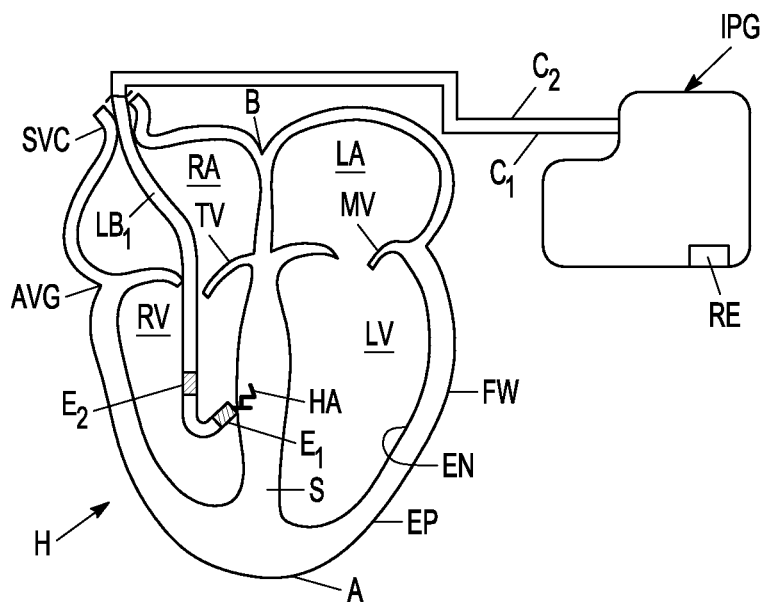
FIG. 7A is the view of FIG. 1 showing a conventional active fixation lead with a helix for attachment of the tip electrode to a septal wall.
Figure 7B:
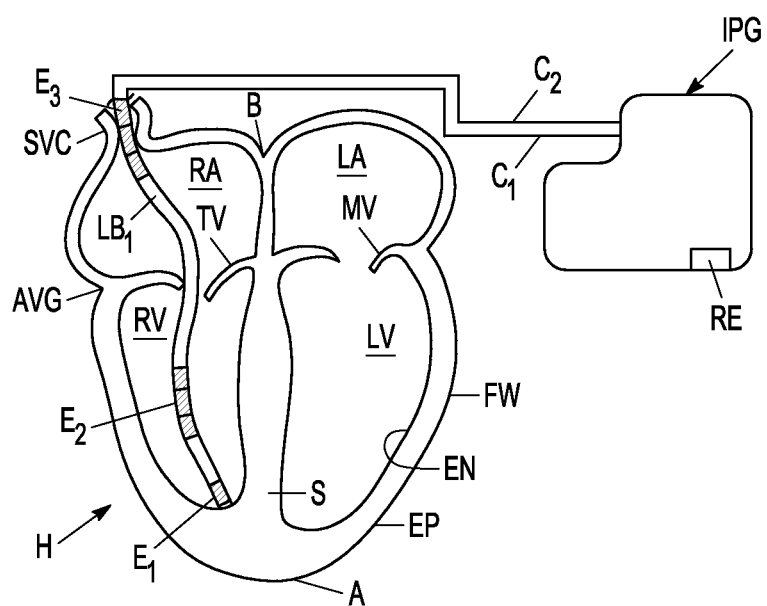
FIG. 7B is the view of FIG. 1 showing a shocking electrode.

In addition, the catheter $LB_5$ within the right ventricle can have multiple electrodes along its length (as shown in FIG. 7). Individual pairs of these electrodes $E_1$-$E_4$ can be switched on or off over time so that the appropriate pair of electrodes within the right ventricle is selected for optimized left ventricular pacing.

Figure 19:
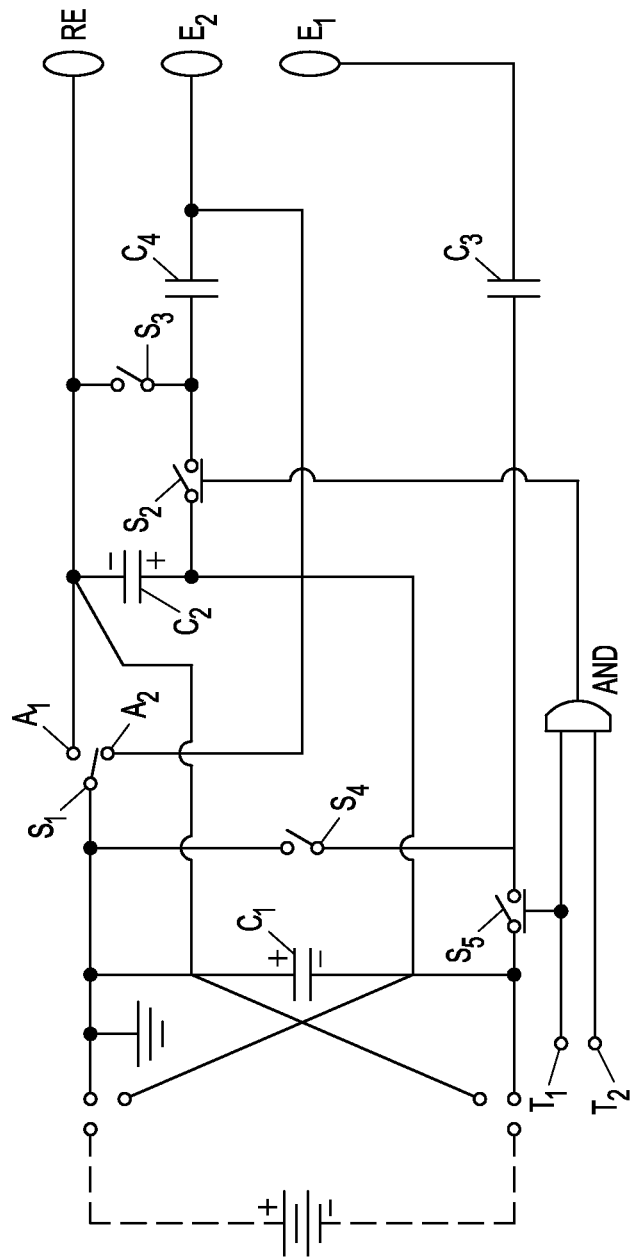
FIG. 19 is an electrical schematic for a portion of a pacing output desired in a pulse generator with programmable pacing configurations.

FIG. 19 illustrates a representative circuit in schematic format for a portion of a cardiac stimulation pulse generator that is capable of providing pacing output for either the conventional design or the present invention. The circuit of FIG. 19 could be for an implantable pacemaker or any external stimulation system for diagnostic or therapeutic use.

The stimulation device has three output terminals that are connected to three electrodes $E_1$, $E_2$, RE in the body. Electrodes $E_1$, $E_2$ are positioned in the right ventricle RV with it being preferred that at least one of these electrodes be in direct contact with the septum S.

The reference electrode RE is an indifferent electrode which can be connected electronically to the housing of the implantable pulse generator IPG. The reference electrode RE may be an electrode directly on the implantable pulse generator or any other electrode for placement inside or outside of the heart as described above.

Figure 17:
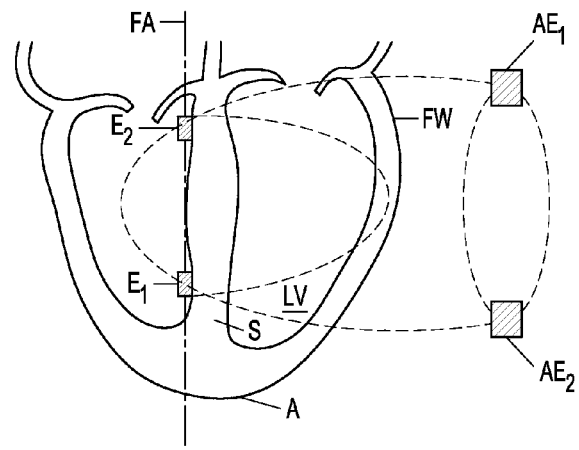
FIG. 17 is the view of FIG. 15 with a reference electrode replaced by two polarized electrodes.

In the preferred embodiment, the reference electrode is grounded to the housing of the implantable pulse generator. FIG. 17 illustrates an alternative embodiment where the reference electrode includes two active electrodes $AE_1$, $AE_2$ external to the heart. The active electrodes $AE_1$, $AE_2$ are paced with pulsed waveforms which are polar opposites of the waveforms on electrodes $E_1$, $E_2$. This creates dual uni-polar field $F_1$, $F_2$ in addition to the left field lines LFL previously described.

In the Figure, the amplitude of the waveforms from FIG. 18 (or other waveform as described) is shown in phantom lines as the battery voltage applied to the four poles on the left of FIG. 19 to charge the two pacing capacitors $C_1$ and $C_2$. Details of the charging circuitry as well as other controlling circuitry for pacing and sensing are omitted for ease of illustration, but should be customary to those skilled in the art. Only capacitor $C_1$ needs to be charged for the conventional pacing output, whereas both C1 and C2 need to be charged for the present invention. Capacitor $C_3$ and $C_4$ are for the pacing output coupling to the patient. For ease of illustration and explanation, the output waveform from FIG. 18 with the same amplitude and simultaneous timing is assumed for the design schematic in FIG. 19. A switch $S_1$ permits selection between unipolar conventional pacing and pacing according to the present invention (by contact with switch pole $A_1$) or bi-polar conventional pacing (by contact with switch pole $A_2$). Selection between conventional pacing or the present invention is made by applying a digital signal with the timing information as shown in FIG. 18 to either $T_1$ or $T_1$ and $T_2$, namely to either toggle the switch $S_5$ or $S_2$ and $S_5$ simultaneously). An AND gate is used to allow the close of the switch $S_2$ only for pacing according to the present invention. Switches $S_3$ and $S_4$ permit re-neutralizing the pacing charges at the patient-electrode interface.

As is customary with implantable pulse generators, the device may be programmable to achieve either conventional bipolar or unipolar stimulation or to achieve the stimulation of the present invention through an external programmer or controlled automatically by the device. The selection can be based on user preference or be driven by physiological factors such as widths of the patient's QRS complex or the conduction interval between the stimulus to a far away region in the heart. In addition switching between the pacing of the present invention and conventional pacing can also be determined by the percentage of pacing with a preference for a higher percentage with the pacing of the present invention. Further, the switching from the conventional pacing to the present invention pacing can be used when there exists an exit block or the pacing electrode is located in infracted myocardium when conventional pacing can not effect the depolarization of the myocardium at the high output level. The automatic determination can be effected through the deployment of any automatic capture detection technology that exists in the prior art. Additionally, wireless network enabled switching function for therapy optimization can also be implemented with the present invention. In such case, certain patient physiologic data are gathered by the implantable device and sent to a remote server/monitor through a wireless communication network.

FIG. 18 illustrates a preferred waveform with electrodes $E_1$, $E_2$ being simultaneously pulsed with opposite polarity.

Figure 18A:
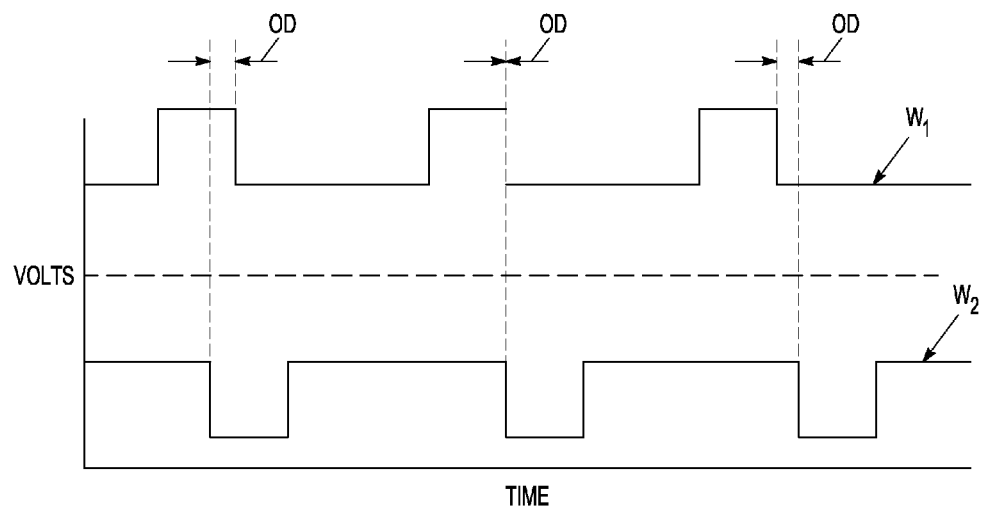
FIG. 18A is a view similar to that of FIG. 18 showing alternative waveforms.
Figure 18B:
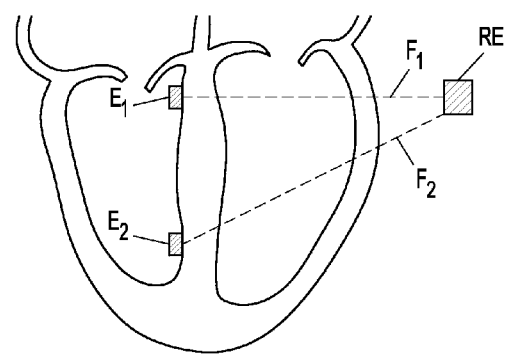
FIG. 18B is a view similar to FIG. 18 and showing two electrodes creating two separate fields to a reference electrode.

FIG. 18A illustrates waveforms $W_1'$, $W_2'$ of similar structure to the waveforms of FIG. 18 but slightly out of phase to present a partial overlap duration DO. With FIG. 18A at least a portion of time includes a monopolar pacing from individual ones of the electrodes $E_1$, $E_2$ to the reference electrode RE. This pacing creates out of phase monopolar fields $F_1$, $F_2$ as illustrated in FIG. 18B. While the amplitudes of the two waveforms are shown equal, they need not be equal in practice.

The present invention can also be extended to the defibrillation therapy where high-energy pulses with various waveforms are delivered through electrode systems to treat tachycardia and fibrillation (both atrium and ventricle). The present invention is believed to be able to achieve lower defibrillation threshold due to better distribution of the electrical field, causing higher voltage gradient at least in certain parts of the heart compared to that by the conventional defibrillation configuration as seen in FIG. 7B. Additionally, the present invention can be used to perform anti-tachy pacing where faster than conventional pacing pulse sequences are used to stop certain tachyarrhythmia. The present invention is believed to be advantageous due to the wider coverage of the electrical field and the capability of capturing special conductions system in the heart (both atrium and ventricle).

Figure 20:
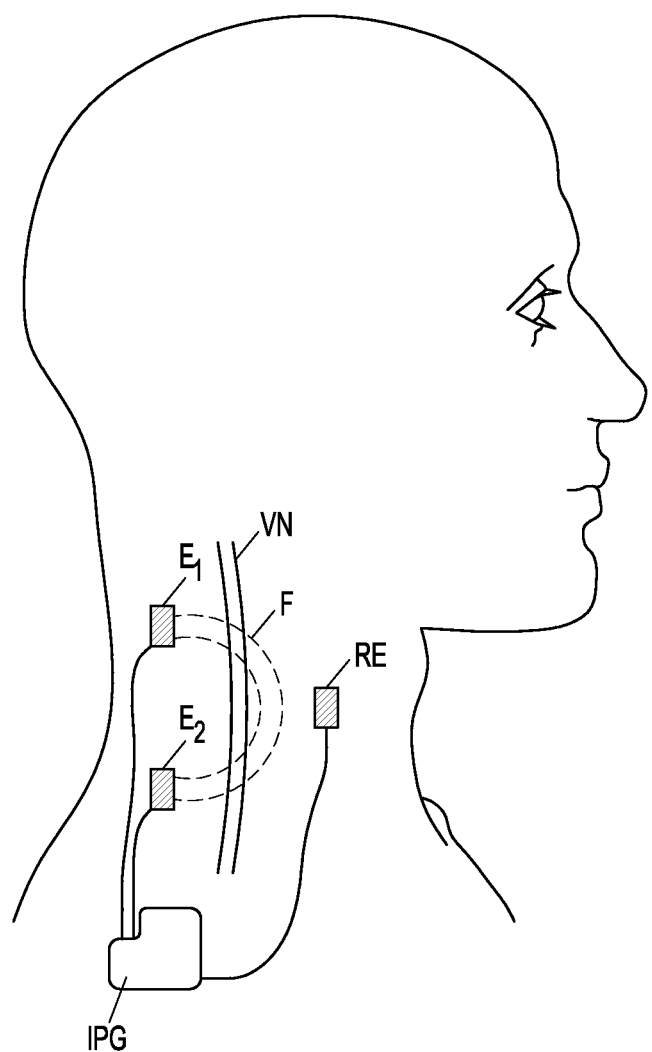
FIG. 20 is a side elevation view of a patient's head and neck showing application of the present invention directed to applying a pacing signal to a vagus nerve.

While cardiac applications are a most preferred embodiment, the present application is applicable to other therapies where high current density spot(s) away from the electrodes are beneficial for stimulating the target, including but not limited to nerves, muscle, gastric and intestine system, and cortex). For example, U.S. Pat. No. 5,299,569 to Wernicke et al. issued Apr. 5, 1994 (and incorporated herein by reference is one of a number of patents assigned to Cyberonics, Inc. describes pacing the vagus nerve to treat a wide variety of disorders. Pacing electrodes are applied directly to the vagus nerve in, for example, the neck. Application of an electrode directly to the vagus nerve creates risk of mechanical injury (e.g., pressure necrosis) to the nerve. FIG. 20 illustrates use of the present invention in such application. Electrodes $E_1$, $E_2$ are placed subcutaneously near (trancutaneously or transvenously coupled) but not on the vagus nerve VN in the neck. A reference electrode RE is placed subcutaneously (trancutaneously or transvenously coupled) on an opposite side of the nerve VN. The electrodes $E_1$, $E_2$ and RE are connected to a pulse generator IPG. With signals as described above, the resulting field F captures the vagus nerve. The signals may be selected to have amplitude, frequency and other parameters as more fully described in the '569 patent. It will be appreciated that other alternative examples of using the present invention to pace an organ or the nerve will occur to one of ordinary skill in the art with the benefit of the teachings of the present invention.

It has been shown how the objects of the invention have been achieved in a preferred embodiment. Modifications and equivalents of the disclosed concepts are intended to be included within the scope of the claims appended hereto.

What is claimed is:

1. An implantable medical device comprising:
   a signal generator configured to:
      provide a first electrostimulation energy to a first electrode disposed in a right ventricle of a heart, the first electrostimulation energy having a first potential relative to a reference potential at a first reference electrode; and
      provide a second electrostimulation energy to a second electrode disposed in the right ventricle of the heart, the second electrostimulation energy having a second potential relative to the reference potential at the reference electrode;

wherein the first and second electrostimulation energies comprise at least partially overlapping, opposite polarity electrostimulation energies with respect to the reference potential; and wherein one of the first and second electrodes is configured to be secured to a target location near a bundle of His.

2. The implantable medical device of claim 1, comprising the first electrode the second electrode, and the first reference electrode.

3. The implantable medical device of claim 2, wherein the signal generator is configured to be coupled to at least one of the first and second electrodes being disposed in the right ventricle and being secured to the septum of the heart.

4. The implantable medical device of claim 2, wherein the signal generator is configured to be coupled to at least one of the first and second electrodes being disposed in the right ventricle and being secured near the tricuspid valve of the right ventricle.

5. The implantable medical device of claim 2, wherein the signal generator is configured to be coupled to the first reference electrode being disposed remote from the heart.

6. The implantable medical device of claim 2, wherein the signal generator is configured to be coupled to the first reference electrode disposed on a housing of the implantable medical device.

7. The implantable medical device of claim 2, wherein the signal generator is configured to be coupled to a first reference electrode being disposed in one of a left ventricle, a tissue of the free wall of the left ventricle, on the epicardial surface of the left ventricle, or in a coronary sinus.

8. The implantable medical device of claim 2, comprising a second reference electrode and a switch configured to select one of the first and second reference electrodes.

9. The implantable medical device of claim 1, comprising an electrode configured to be disposed in an atrium of the heart to facilitate atrial-ventricular sequential pacing.

10. The implantable medical device of claim 1, comprising a defibrillation lead system with at least one shock electrode and circuitry configured for energizing the defibrillation lead system for defibrillation therapy.

11. The implantable medical device of claim 1, wherein the signal generator is configured to provide the first and second electrostimulation energies to a selected area near or at the septum of the heart for treating a bundle branch block.

12. The implantable medical device of claim 1, wherein the one of the first and second electrodes is sized and shaped to be secured to the septum of the heart at the bundle of His, and wherein the other one of the first and second electrodes is sized and shaped to be secured at or near an apex of the right ventricle of the heart.

13. A method for providing a therapy to treat a bundle branch block of a heart, the method comprising:

generating a pacing signal that includes first and second signal components having opposite polarity and at least partially overlapping in time, wherein the first and second signal components have a potential relative to at least one of multiple reference electrodes placed subcutaneously in or near the heart;

applying the pacing signal to the heart using first and second electrodes in or near a right ventricle of the heart and at least one of the multiple refrence electrodes; and identifying a patient physiological response to the applied pacing signal;

wherein identifying the patient physiological response includes identifying a ventricular contraction of the heart in the presence of a bundle branch block.

14. The method of claim 13, wherein applying the pacing signal to the heart comprises:

applying a first pacing signal to the heart using a first one of the multiple reference electrodes; and applying a second pacing signal o the heart using a different second one of the multiple reference electrodes;

wherein identifying the patient physiological response to the applied pacing signal comprises identifying a patient physiological response that corresponds to each of the first and second pacing signals.

15. The method of claim 13, wherein applying the pacing signal to the heart using the first and second electrodes comprises applying the pacing signal to a target location near a bundle of His using one of the first and second electrodes secured to the target location.

16. The method of claim 13, wherein applying the pacing signal includes applying a pacing signal that includes a biphasic component and has a magnitude of less than about 20 volts.

17. The method of claim 13, wherein applying the pacing signal comprises using at least one of the first and second electrodes near the tricuspid valve.

18. The method of claim 13, comprising using a refrence electrode more proximate to a signal generator than the heart, wherein the signal generator is configured to generate the pacing signal.

19. The method of claim 13, wherein generating the pacing signal that includes first and second signal components includes generating a pacing signal that includes first and second signal components that have different signal magnitudes.

20. An implantable medical device configured to treat a bundle branch block, the implantable medical device comprising:

a signal generator configured to:

provide a first electrostimulation energy to a first electrode that is configured to be secured to a heart wall near a bundle of His of the heart and near the tricuspid valve of the heart, the first electrostimulation energy having a first potential relative to a reference potential at a reference electrode; and provide a second electrostimulation energy to a second electrode disposed in or near the right ventricle of the heart, the second electrostimulation energy having a second potential relative to the reference potential at the reference electrode;

wherein the first and second electrostimulation energies comprise at least partially overlapping, opposite polarity electrostimulation energies with respect to the reference potential, and wherein one of the first and second electrostimulation energies comprises a biphasic signal component.

* * * * *